(12) United States Patent
Bevis et al.

(10) Patent No.: US 8,664,471 B2
(45) Date of Patent: *Mar. 4, 2014

(54) RAPIDLY MATURING FLUORESCENT PROTEINS AND METHODS FOR USING THE SAME

(75) Inventors: Brooke Bevis, Somerville, MA (US); Benjamin Glick, Chicago, IL (US)

(73) Assignees: The University of Chicago, Chicago, IL (US); The University of Washington, Seattle, WA (US)

( * ) Notice: Subject to any disclaimer, the term of this patent is extended or adjusted under 35 U.S.C. 154(b) by 1177 days.

This patent is subject to a terminal disclaimer.

(21) Appl. No.: 10/844,064

(22) Filed: May 11, 2004

(65) Prior Publication Data
US 2005/0149994 A1 Jul. 7, 2005

Related U.S. Application Data

(63) Continuation of application No. PCT/US02/40539, filed on Dec. 18, 2002.

(60) Provisional application No. 60/341,723, filed on Dec. 19, 2001.

(51) Int. Cl.
| | | |
|---|---|---|
| A01K 67/00 | (2006.01) | |
| A01K 67/033 | (2006.01) | |
| C07H 21/02 | (2006.01) | |
| C07H 21/04 | (2006.01) | |

(52) U.S. Cl.
USPC .......................... 800/13; 536/23.1; 536/23.5

(58) Field of Classification Search
None
See application file for complete search history.

(56) References Cited

U.S. PATENT DOCUMENTS

| | | |
|---|---|---|
| 972,638 A | 10/1910 | Pease et al. |
| 4,302,536 A | 11/1981 | Longenecker |
| RE30,985 E | 6/1982 | Cartaua |
| 4,399,216 A | 8/1983 | Axel et al. |
| 4,551,433 A | 11/1985 | DeBoer |
| 4,560,655 A | 12/1985 | Baker |
| 4,657,866 A | 4/1987 | Kumar |
| 4,683,195 A | 7/1987 | Mullis et al. |
| 4,683,202 A | 7/1987 | Mullis |
| 4,745,051 A | 5/1988 | Smith et al. |
| 4,767,704 A | 8/1988 | Cleveland et al. |
| 4,837,148 A | 6/1989 | Cregg |
| 4,927,762 A | 5/1990 | Darfler |
| 4,929,555 A | 5/1990 | Cregg et al. |
| 5,182,202 A | 1/1993 | Kajiyama et al. |
| 5,221,623 A | 6/1993 | Legocki et al. |
| 5,229,285 A | 7/1993 | Kajiyama et al. |
| 5,330,906 A | 7/1994 | Kajiyama et al. |
| 5,418,155 A | 5/1995 | Cormier et al. |
| 5,439,797 A | 8/1995 | Tsien et al. |
| 5,484,956 A | 1/1996 | Lundquist et al. |
| 5,491,084 A | 2/1996 | Chalfie et al. |
| 5,538,879 A | 7/1996 | Muller-Rober et al. |
| 5,576,198 A | 11/1996 | McBride et al. |
| 5,595,896 A | 1/1997 | Coruzzi et al. |
| 5,618,722 A | 4/1997 | Zenno et al. |
| 5,629,470 A | 5/1997 | Lam et al. |
| 5,633,155 A | 5/1997 | Kim et al. |
| 5,641,670 A | 6/1997 | Treco et al. |
| 5,650,135 A | 7/1997 | Contag et al. |
| 5,654,173 A | 8/1997 | Jacobs et al. |
| 5,656,466 A | 8/1997 | Moon et al. |
| 5,674,713 A | 10/1997 | McElroy et al. |
| 5,674,731 A | 10/1997 | Lin et al. |
| 5,688,648 A | 11/1997 | Mathies et al. |
| 5,689,045 A | 11/1997 | Logemann et al. |
| 5,689,049 A | 11/1997 | Cigan et al. |
| 5,700,673 A | 12/1997 | McElroy et al. |
| 5,707,804 A | 1/1998 | Mathies et al. |
| 5,728,528 A | 3/1998 | Mathies et al. |

(Continued)

FOREIGN PATENT DOCUMENTS

| | | |
|---|---|---|
| EP | 0036776 | 9/1981 |
| EP | 0155476 | 9/1985 |

(Continued)

OTHER PUBLICATIONS

Ju et al. (1991) Conversion of the interleukin 1 receptor antagonist into an agonist by site-specific mutagenesis. Proc. Natl. Acad. Sci. USA 88: 2658-2662.*

(Continued)

Primary Examiner — Anne-Marie Falk
(74) Attorney, Agent, or Firm — Valauskas Corder LLC

(57) ABSTRACT

Nucleic acid compositions encoding rapidly maturing fluorescent proteins, as well as non-aggregating versions thereof (and mutants thereof) as well as the proteins encoding the same, are provided. The proteins of interest are proteins that are fluorescent, where this feature arises from the interaction of two or more residues of the protein. The subject proteins are further characterized in that, in certain embodiments, they are mutants of wild type proteins that are obtained either from non-bioluminescent *Cnidarian*, e.g., *Anthozoan*, species or are obtained from *Anthozoan* non-*Pennatulacean* (sea pen) species. In certain embodiments, the subject proteins are mutants of wild type *Discosoma* sp. "red" fluorescent protein. Also of interest are proteins that are substantially similar to, or mutants of, the above specific proteins. Also provided are fragments of the nucleic acids and the peptides encoded thereby, as well as antibodies to the subject proteins and transgenic cells and organisms. The subject protein and nucleic acid compositions find use in a variety of different applications. Finally, kits for use in such applications, e.g., that include the subject nucleic acid compositions, are provided.

30 Claims, 4 Drawing Sheets

(56) References Cited

U.S. PATENT DOCUMENTS

| | | | |
|---|---|---|---|
| 5,733,761 | A | 3/1998 | Treco et al. |
| 5,739,409 | A | 4/1998 | Fischer et al. |
| 5,750,870 | A | 5/1998 | Mathews et al. |
| 5,767,367 | A | 6/1998 | Dudits et al. |
| 5,795,737 | A | 8/1998 | Seed et al. |
| 5,804,387 | A | 9/1998 | Cormack et al. |
| 5,824,485 | A | 10/1998 | Thompson et al. |
| 5,843,746 | A | 12/1998 | Tatsumi et al. |
| 5,863,727 | A | 1/1999 | Lee et al. |
| 5,866,336 | A | 2/1999 | Nazarenko et al. |
| 5,869,255 | A | 2/1999 | Mathies et al. |
| 5,874,304 | A | 2/1999 | Zolotukhin et al. |
| 5,911,952 | A | 6/1999 | Tsuji |
| 5,919,445 | A | 7/1999 | Chao |
| 5,945,283 | A | 8/1999 | Kwok et al. |
| 5,945,526 | A | 8/1999 | Lee et al. |
| 5,958,713 | A | 9/1999 | Thastrup et al. |
| 5,968,738 | A | 10/1999 | Anderson et al. |
| 5,968,750 | A | 10/1999 | Zolotukhin et al. |
| 5,976,796 | A | 11/1999 | Szalay et al. |
| 5,981,200 | A | 11/1999 | Tsien et al. |
| 5,985,577 | A | 11/1999 | Bulinski |
| 5,989,835 | A | 11/1999 | Dunlay et al. |
| 5,998,146 | A | 12/1999 | Latva et al. |
| 6,008,373 | A | 12/1999 | Waggoner et al. |
| 6,020,192 | A | 2/2000 | Muzyczka et al. |
| 6,066,476 | A | 5/2000 | Tsien et al. |
| 6,130,313 | A | 10/2000 | Li et al. |
| 6,306,600 | B1 | 10/2001 | Kain et al. |
| 7,671,185 | B2 * | 3/2010 | Glick et al. .................. 536/23.1 |
| 7,910,714 | B2 * | 3/2011 | Glick et al. .................. 536/23.1 |
| 2002/0197676 | A1 | 12/2002 | Lukyanov et al. |
| 2003/0059835 | A1 | 3/2003 | Tsien et al. |
| 2003/0170911 | A1 | 9/2003 | Tsien et al. |

FOREIGN PATENT DOCUMENTS

| | | |
|---|---|---|
| EP | 0127839 | 7/1992 |
| EP | 0244234 | 7/1993 |
| WO | WO 87/00195 | 1/1987 |
| WO | WO 90/03430 | 4/1990 |
| WO | WO 90/04036 | 4/1990 |
| WO | WO 90/10077 | 9/1990 |
| WO | WO 91/00357 | 1/1991 |
| WO | WO 92/02190 | 2/1992 |
| WO | WO 99/15650 | 4/1999 |
| WO | WO 99/49019 | 9/1999 |
| WO | WO 00/02997 | 1/2000 |
| WO | WO 00/03246 | 1/2000 |
| WO | WO 00/17624 | 3/2000 |
| WO | WO 00/17643 | 3/2000 |
| WO | WO 00/26408 | 5/2000 |
| WO | WO 00/46233 | 8/2000 |
| WO | WO 01/27150 | 4/2001 |
| WO | WO 02/068459 | 9/2002 |
| WO | WO 02/40539 | 5/2003 |

OTHER PUBLICATIONS

Pakula et al. (1989) Genetic analysis of protein stability and function. Annu. Rev. Genet. 23: 289-310.*

Skolnick et al. (2000) From genes to protein structure and function: novel applications of computational approaches in the genomic era. TIBTECH 18: 34-39.*

Witkowski et al. (1999) Conversion of a beta-ketoacyl synthase to a malonyl decarboxylase by replacement of the active-site cysteine with glutamine. Biochemistry 38: 11643-11650.*

Fischer, et al., "A Brilliant Monomeric Red Fluorescent Protein to Visualize Cytoskeleton Dynamics in *Dictyostelium*," *FEBS Letters*, (2004) 577:227-232.

Knop et al., "Improved Version of the Red Fluorescent Protein (drFP583/DsRed/RFP)," *BioTechniques*, (2002) 33:3:592, 594, 596-598, 600, 602.

Altschul, S.F. et al., "Basic Local Alignment Search Tool," J. Mol. Biol. (1990) 215:403-410.

Anderluh, G. et al., "Cloning, Sequencing, and Expression of Equinatoxin II," Biochem. Biophys. Res. Comm. (1996) 220:437-442.

Atwell, S. et al., "Structural Plasticity in a Remodeled Protein-Protein Interface," *Science* (1997) 278:1125-1128.

Baird, G.S. et al., "Biochemistry, Mutagenesis, and Oligomerization of Dsred, a Red Fluorescent Protein From Coral," Proc. Natl. Acad. Sci. USA (2000) 97:11984-11989.

Ballance, D.J. et al., "Transformation of *Aspergillus nidulans* by the Orotidine-5'-Phosphate Decarboxylase Gene of *Neurospora crassa*," Biochem. Biophys. Res. Comm. (1983) 112(1):284-289.

Barton, M.C. et al., "Site-directed, recombination-mediated mutagenesis of a complex gene locus," Nucleic Acids Res. (1990) 18(24):7349-7355.

Beach, D. et al., "Functionally homologous cell cycle control genes in budding and fission yeast," Nature (1982) 300:706-709.

Beernink, P.T. and Tolan, D.R., "Disruption of the aldolase A tetramer into catalytically active monomers," *Proc. Natl. Acad. Sci. USA* (1996) 93:5374-5379.

Bevis, B.J. and Glick, B.S., "Rapidly maturing variants of the *Discosoma* red fluorescent protein (DsRed)," Nat. Biotechnol. (2002) 20:83-87.

Bogan, A.A. and Thorn, K.S., "Anatomy of hot spots in protein interfaces," *J. Mol. Biol.* (1998) 280:1-9.

Boshart, M. et al., "A very strong enhancer is located upstream of an immediate early gene of human cytomegalovirus," Cell (1985) 41:521-530.

Cadwell, R.C. and Joyce, G.F., "Mutagenic PCR," PCR Primer, A Laboratory Manual (1995) Dieffenbach and Dveksler, eds., Cold Spring Harbor Laboratory Press, 583-589.

Campbell, R.E. et al., "A monomeric red fluorescent protein," Proc. Natl. Acad. Sci. USA (2002) 99(12):7877-7882.

Carbonell, L.F. et al., "Synthesis of a gene coding for an insect-specific scorpion neurotoxin and attempts to express it using baculovirus vectors," Gene (1988) 73:409-418.

Colicelli, J. et al., "A temperature-sensitive mutation constructed by 'linker insertion' mutagenesis," Mol. Gen. Genet. (1985) 199:537-539.

Condeelis, J.S. et al., "Imaging of cancer invasion and metastasis using green fluorescent protein," *Eur. J. Cancer* (2000) 36:1671-1680.

Cormack, B.P. et al., "FACS-optimized mutants of the green fluorescent protein (GFP)," *Gene* (1996) 173:33-38.

Cregg, J.M. et al., "Pichia pastoris as a host system for transformations," Mol. Cell Biol. (1985) 5(12):3376-3385.

Cronin, S. and Hampton, R., "A genetics-friendly GFP assay," *Trends Cell Biol.* (1999) 9:36.

Cubitt, A.B. et al., "Understanding structure-function relationships in the *Aequoria victoria* green fluorescent protein," *Green Fluorescent Proteins (Methods in Cell Biology)* (1999), Sullivan and Kay, eds, Academic Press, San Diego, 58:19-30.

Das, S. et al., "Transformation of *Kluyveromyces fragilis*," J. Bacteriol. (1984) 158(3):1165-1167.

Davidow, L.S. et al., "Integrative transformation of the yeast *Yarrowia lipolytica*," Curr. Genet. (1985) 10:39-48.

De Boer, H.A. et al., "The *tac* promoter: A functional hybrid derived from the trp and *lac* promoters," Proc. Natl. Acad. Sci. USA (1983) 80:21-25.

De Giorgi, F. et al., "Targeting GFP to organelles," *Green Fluorescent Proteins (Methods in Cell Biology)* (1999), Sullivan and Kay, eds., Academic Press, San Diego, 58:75-85.

De Louvencourt, L. et al., "Transformation of *Kluyveromyces lactis* by killer plasmid DNA," J. Bacteriol. (1983) 154(2):737-742.

Demeler, B. and Saber, H., "Determination of molecular parameters by fitting sedimentation data to finite-element solutions of the Lamm equation," *Biophys. J.*. (1998) 74:444-454.

Deo, S.K. and Daunert, S., "Luminescent proteins from Aequorea victoria: applications in drug discovery and in high throughput analysis," *Fresenius J. Anal. Chem.* (2001) 369:258-266.

(56) References Cited

OTHER PUBLICATIONS

Dickson, R.M. et al., "On/off blinking and switching behavior of single molecules of green fluorescent protein," *Nature* (1997) 388:355-358.
Dijkema, R. et al., "Cloning and expression of the chromosomal immune interferon gene of the rat," EMBO J. (1985) 4(3):761-767.
Dittrich, P. et al., "Accessing molecular dynamics in cells by fluorescence correlation spectroscopy," *Biol. Chem.* (2001) 382:491-494.
Dove, S.G. et al., "Isolation and partial characterization of the pink and blue pigments of pocilloporid and acroporid corals," Biol. Bull. (1995) 189:288-297.
Ellenberg, J. et al., "Dual-color imaging with GFP variants," *Trends Cell Biol.*(1999) 9:52-56.
Fradkov, A.F. et al., "Novel fluorescent protein from *Discosoma* coral and its mutants possesses a unique far-red fluorescence," FEBS Lett. (2000) 479:127-130.
Friesen, P.D. and Miller, L.K., "The regulation of baculovirus gene expression," Current Topics in Microbiology and Immunology, (1986) 131:32-49.
Garcia-Parajo, M.F. et al., "The nature of fluorescence emission in the red fluorescent protein DsRed, revealed by single-molecule detection," *Proc. Natl. Acad. Sci. USA* (2001) 98:14392-14397.
Garcia-Parajo, M.F. et al., "Visualizing individual green fluorescent proteins with a near field optical microscope," *Cytometry* (1999) 36:239-246.
Gleeson, M.A. et al., "Transformation of the methylotrophic yeast *hansenula polymorpha*," J. Gen. Microbiol. (1986) 132:3459-3465.
Goeddel, D.V. et al., "Direct expression in *Escherichia coli* of a DNA sequence coding for human growth hormone," Nature (1979) 281:544-548.
Goeddel, D.V. et al., "Synthesis of human fibroblast interferon by *E. coli*," Nucleic Acids Res. (1980) 8:18:4057-4073.
Gorman, C.M. et al., "The Rous sarcoma virus long terminal repeat is a strong promoter when introduced into a variety of eukaryotic cells by DNA-mediated transfection," Proc. Natl. Acad. Sci. USA (1982) 79:6777-6781.
Gross, L.A. et al., "The structure of the chromophore within DsRed, a red fluorescent protein from coral," *Proc. Natl. Acad. Sci. USA* (2000) 97:22:11990-11995.
Grosschedl, R. and Baltimore, D., "Cell-type specificity of immunoglobulin gene expression is regulated by at least three DNA sequence elements," Cell (1985) 41:885-897.
Gurskaya, N.G. et al., "Color transitions in coral's fluorescent proteins by site-directed mutagenesis," BMC Biochem. (2001) 2:6 pages.
Gurskaya, N.G. et al., "GFP-like chromoproteins as a source of far-red fluorescent proteins," FEBS Lett. (2001) 507:16-20.
Gustin, K.E. and Burk, R.D., "A rapid method for generating linker scanning mutants utilizing PCR," Biotechniques (1993) 14:1:22-23.
Harms, G.S. et al., "Autofluorescent proteins in single-molecule research: applications to live cell imaging microscopy," *Biophys. J.* (2001) 80:2396-2408.
Hastings, J.W., "Bioluminescence," Cell Physiology (1995), N. Speralakis, ed, New York, Academic Press, 665-681.
Haugwitz, M. et al., "Characterization of the improved red fluorescent protein DsRed2," Soc. for Neuroscience Abstracts(2001) 27(1):351.
Hawley, T.S. et al., "Four-color flow cytometric detection of retrovirally expressed red, yellow, green, and cyan fluorescent proteins," *Bio Techniques* (2001) 30:1028-1033.
Heim, R. et al., "Improved green fluorescence," *Nature* (1995) 373:663-664.
Heim, R. and Tsien, R.Y., "Engineering green fluorescent protein for improved brightness, longer wavelengths and fluorescence resonance energy transfer," *Curr. Biol.*(1996) 6:2:178-182.
Higgins, D.G. and Sharp, P.M., "Fast and sensitive multiple sequence alignments on a microcomputer," CABIOS Comm. (1989) 5(2):151-153.
Hinnen, A. et al., "Transformation of yeast," Proc. Natl. Acad. Sci. USA (1978) 75(4):1929-1933.
Hu, J.C., "Repressor fusions as a tool to study protein-protein interactions," *Structure* (1995) 3:5:431-433.
Ito, H. et al., "Transformation of intact yeast cells treated with alkali cations," J. Bacteriol. (1983) 153(1):163-168.
"IUPAC-IUB commission on biochemical nomenclature a one-letter notation for amino acid sequences tentative rules," J. Biol. Chem. (1968) 243(13):3557-3559.
Jakobs, S. et al., "EGFP and DsRed expressing cultures of *Escherichia coli* imaged by confocal, two-photon and fluorescence lifetime microscopy," *FEBS Lett.* (2000) 479:131-135.
Jones, D.H. and Winistorfer, S.C., "Recombinant circle PCR and recombination PCR for site-specific mutagenesis without PCR product purification," Biotechniques (1992) 12(4):528-533.
Jost, C.R. et al., "Mammalian expression and secretion of functional single-chain Fv molecules," J. Biol. Chem. (1994) 269(42):26267-26273.
Kelly, J.M. and Hynes, M.J., "Transformation of *aspergillus niger* by the amdS gene of *Aspergillus nidulans*," Embo J. (1985) 4(2):475-479.
Kilgard et al., "Anticipated stimuli across skin," *Nature* 373:663.
Klebanoff, S. et al., "Metabolic similarities between fertilization and phagocytosis. Conservation of peroxidatic mechanism," J. Exp. Med. (1979) 149:938-953.
Kubitscheck, U. et al., "Imaging and tracking of single GFP molecules in solution," *Biophys. J.* (2000) 78:2170-2179.
Kunze, G. et al., "Transformation of the industrially important yeasts *Candida maltose* and *Pichia guilliermondii*," J. Basic Microbiol. (1985) 25:2:141-144.
Kurtz, M.B. et al., "Integrative transformation of *Candida albicans*, using a cloned *candida* ADE2 gene," Mol. Cell Biol. (1986) 6:1:142-149.
Laitinen, O.H. et al., "Biotin induces tetramerization of a recombinant monomeric avidin. A model for protein-protein interactions," *J. Biol. Chem.* (2001) 276:8219-8224.
Laue, T.M. and Stafford, W.F., "Modern applications of analytical ultracentrifugation," *Annu. Rev. Biophys. Biomol. Struct.* (1999) 28:75-100.
Lauf, U. et al., "Expression of fluorescently tagged connexins: a novel approach to rescue function of oligomeric DsRed-tagged proteins," *FEBS Lett.* (2001) 498-11-15.
Lee, S.H. and Camilli, A., "Novel approaches to monitor bacterial gene expression in infected tissue and host," *Curr. Opin. Microbiol.* (2000) 3:97-101.
Liu, A.Y. et al., "Chimeric mouse-human IgG1 antibody that can mediate lysis of cancer cells," Proc. Natl. Acad. Sci. USA (1987) 84:3439-3443.
Liu, A.Y. et al., "Production of a mouse-human chimeric monoclonal antibody to CD20 with potent Fc-dependent biologic activity," J. Immunol. (1987) 139(10):3521-3526.
Luckow, V.A. and Summers, M.D., "Trends in the development of baculovirus expression vectors," Bio/Technology (1988) 6:47-55.
Lukyanov, K. et al., "Natural animal coloration can be determined by a nonfluroescent green fluorescent protein homolog," J. Biol. Chem. (2000) 275(34):25879-25882.
Macek, P. et al., "Intrinsic tryptophan fluorescence of equinatoxin II, a pore-forming polypeptide from the sea anemone *Actinia equina* L, monitors its interaction with lipid membranes," Eur. J. Biochem. (1995) 234:329-335.
Maeda, S. et al., "Production of human α-interferon in silkworm using a baculovirus vector," Nature (1985) 315:592-594.
Marotti , K.R. and Tomich, C-S.C., "Simple and efficient oligonucleotide-directed mutagenesis using one primer and circular plasmid DNA template," Gene Anal. Tech. (1989) 6:67-70.
Martin, B.M. et al., "Glycosylation and processing of high levels of active human glucocerebrosidase in invertebrate cells using a baculovirus expression vector," DNA (1988) 7(2):99-106.
Martynov, V.I. et al., "Alternative cyclization in GFP-like proteins family," J. Biol. Chem. (2001) 276:24:21012-21016.
Matz, M.V. et al., "Fluorescent proteins from nonbioluminescent Anthozoa species," Nat. Biotechnol. (1999) 17:969-973.
McNew, J.A. et al., "Gos 1p, a *Saccharomyces cerevisiae* SNARE protein involved in Golgi transport," *FEBS Lett.* (1998) 435-89-95.

(56) References Cited

OTHER PUBLICATIONS

McTigue, M.A. et al., "Crystal structures of a schistosomal drug and vaccine target: flutathione S-transferase from *Schistosoma japonica* and its complex with the leading antischistosomal drug praziquantel," *J. Mol. Biol.* (1995) 246:21-27.

Miller, D.W. et al., "An insect baculovirus host-vector system for high-level expression of foreign genes," Genetic Engineering (1986) 8:277-298.

Miyajima, A. et al., "Use of the silkworm, Bombyx mori, and an insect baculovirus vector for high-level expression and secretion of biologically active mouse interleukin-3," Gene (1987) 58:273-281.

Miyawaki, A. et al., "Fluorescent indicators for $Ca^{2+}$based on green fluorescent proteins and calmodulin," *Nature* (1997) 388:882-887.

Moerner, W.E. et al., "Optical methods for exploring dynamics of single copies of green fluorescent protein," *Cytometry* (1999) 36:232-238.

Okayama, H. and Berg, P., "A cDNA cloning vector that permits expression of cDNA inserts in mammalian cells," Mol. Cell Biol. (1983) 3(2):280-289.

Phillips, G.N., Jr., "Structure and dynamics of green fluorescent protein," *Curr. Opin. Struc. Biol.* (1997) 7:821-827.

Pierce, D.W. and Vale, R.D., "Single-molecule fluorescence detection of green fluorescence protein and application to single-protein dynamics," *Green Fluorescent Proteins (Methods in Cell Biology)* (1999) Sullivan and Kay, eds., Academic Press, San Diego 58:49-73.

Piston, D.W., "Imaging living cells and tissues by two-photon excitation microscopy," *Trends Cell Biol.* (1999) 9:66-69.

Plant Biochemistry and Molecular Biology, Lea & Leegood, eds., John Wiley & Sons (1993) 275-295.

Pokkuluri, P.R. et al., "A domain flip as a result of a single amino-acid substitution," *Structure* (1998) 6:8:1067-1073.

Pollok, B.A. and Heim, R., "Using GFP in FRET-based applications," *Trends Cell Biol.* (1999) 9:57-60.

Prentki, P. and Krisch, H.M., "In vitro insertional mutagenesis with a selectable DNA fragment," Gene (1984) 29:303-313.

Radotic, K. et al., "Spontaneous ultraweak bioluminescence in plants: origins, mechanisms and properties," Gen. Physiol. Biophys. (1998) 17:289-308.

Raffen, R. and Stevens, F.J., "Small zone, high-speed gel filtration chromatography to detect protein aggregation associated with light chain pathologies," *Methods Enzymol.* (1999) 309:318-332.

Remington, S.J., "Negotiating the Speed Bumps to Fluorescence," *Nat. Biotechnol.* (2002) 20:28-29.

Roggenkamp, R. et al., "Transformation of the methylotrophic yeast *Hansenula polymorpha* by autonomous replication and integration vectors," Mol. Gen. Genet. (1986) 202:302-308.

Rossanese, O.W. et al., "Golgi structures correlates with transitional endoplasmic reticulum organization in *Pichia pastoris* and *Saccharomyces cerevisiae*," J. Cell Biol. (1999) 145(1):69-81.

Rossanese, O.W. et al., "A role for actin, Cdclp and Myo2p in the inhereitance of late Golgi elements in *Saccharomyces cerevisiae*," *J. Cell Biol.* (2001) 153:47-61.

Sayers, J.R. et al., "Rapid high-efficiency site-directed mutagenesis by the phosphorothioate approach," Biotechniques (1992) 13(4):592-596.

Schomer, B. and Epel, D., "Redox changes during fertilization and maturation of marine invertebrate eggs," Dev. Biol. (1998) 203:1-11.

Schwille, P. et al., "Molecular dynamics in living cells observed by fluorescence correlation spectroscopy with one- and two-photon excitation," *Biophys. J.* (1999) 77:2251-2265.

Siebenlist, U. et al., "*E. coli* RNA polymerase interacts homologously with two different promoters," Cell (1980) 20:269-281.

Sikorski, R.S. and Hieter, P., "A system of shuttle vectors and yeast host strains designed for efficient manipulation of DNA in *Saccharomyces cerevisiae*," Genetics (1989) 122:19-27.

Smith, G.E. et al., "Modification and secretion of human interleukin 2 produced in insect cells by a baculovirus expression vector," Proc. Natl. Acad. Sci. USA (1985) 82:8404-8408.

Smith, D.B. and Johnson, K.S., "Single-step purification of polypeptides expressed in *Escherichia coli* as fusions with glutathione S-transferase," *Gene* (1988) 67:31-40.

Suhadolnik, R.J. et al., "Biochemical Tools for Studying the Structural Requirements for Interaction at the Catalytic and Regulatory Sites of Ribonucleotide Reductase from *Lactobacillus leichmannii*," *J. Biol. Chem.* (1968) 243:12:3532-3537.

Terskikh, A. et al., "Fluorescent Timer: Protein that Changes Color with Time," Science (2000) 290:1585-1588.

Terskikh, A.V. et al., "Analysis of DsRed Mutants. Space Around the Fluorophore Accelerates Fluorescence Development," J. Biol. Chem. (2002) 277(10):7633-7636.

Tilburn, J. et al., "Transformation by integration in *Aspergillus nidulans*," Gene (1983) 26:205-221.

Totsune, H. et al., "Chemiluminescence from Bamboo Shoot Cut," Biochem. Biophys. Res. Comm. (1993) 194(3):1025-1029.

Tsein, R.Y., "The Green Fluorescent Protein," Annu. Rev. Biochem. (1998) 67:509-544.

Tsein, R.Y., "Rosy Dawn for Fluorescent Proteins," Nat. Biotech. (1999) 17:956-957.

Van Den Berg, J.A. et al., "Kluyveromyces as a host for heterologous gene expression: Expression and secretion of prochymosin," Bio/Technology (1990) 8:135-139.

Verkhusha, V.V. et al., "An Enhanced Mutant of Red Fluorescent Protein Dsred For Double Labeling and Developmental Timer of Neutral Fiber Bundle Formation," *J. Biol. Chem.* (2001) 276:32:29621-29624.

Vlak, J.M. et al., "Functional Studies on the P10 Gene of *Autographa Californica* Nuclear Polyhedrosis Virus Using a Recombinant Expressing A P10-B-Galactosidase Fusion Gene," J. Gen. Virol. (1988) 69:765-776.

Wahlfors, J. et al., "Green Fluorescent Protein (GFP) Fusion Constructs in Gene Therapy Research," *Histochem. Cell Biol.* (2001) 115:59-65.

Wall, M.A. et al., "The Structural Basis for Red Fluorescence in the Tetrameric GFP Homolog DsRed," *Nat. Struct. Biol.* (2000) 7:12:1133-1138.

Weiner, M.P. et al., "A Method for the Site-directed Mono- and Multi-mutagenesis of Double-stranded DNA," Gene (1993) 126:35-41.

Weiss, S., "Fluorescence Spectroscopy of Single Biomolecules," *Science* (1999) 283:1676-1683.

Wiehler, J. et al., "Mutants of *Discosoma* Red Fluorescent Protein with a GFP-Like Chromophore," *FEBS Lett.* (2001) 487:384-389.

Wilson, T. and Hastings, J.W., "Bioluminescence," Ann. Rev. Cell Cev. Biol. (1998) 14:197-230.

Yang, T-T. et al., "Optimized Codon Usage and Chromophore Mutations Provide Enhanced Sensitivity with the Green Fluorescent Protein," Nucleic Acids Research (1996) 24(22):4592-4593.

Yanushevich, Y.G. et al., "A Strategy for the Generation of Non-aggregating Mutants of *Anthozoa* Fluorescent Proteins," *FEBS Lett.* (2002) 511:11-14.

Yarbrough, D. et al., "Refined Crystal Structure of DsRed, a Red Fluorescent Protein from Coral, at 2.0-A Resolution," Proc. Natl. Acad. Sci. USA (2001) 98:2:462-467.

Zeng, X. and Hu, J.C., "Detection of Tetramerization Domains in vivo by Cooperative DNA Binding to Tandem 1 Operator Sites," *Gene* (1997) 185:245-249.

Zhu, D., "Oligodeoxynucleotide-Directed Cleavage and Repair of a Single-Stranded Vector: A Method of Site-Specific Mutagenesis," Anal. Biochem. (1989) 177:120-124.

Heikal, A.A. et al., "Molecular spectroscopy and dynamics of intrinsically fluorescent proteins: coral red (dsRed) and yellow (Citrine)," Proc. Natl. Acad. Sci. (2000) 97(22):11986-12001.

Mizuno, H. et al., "Red fluorescent protein from discosoma as a fusion tag and a partner for fluorescence resonance energy transfer," Biochem. (2001) 40:2502-2510.

* cited by examiner

SEQUENCE LISTING

<160> NUMBER OF SEQ ID NOS: 3

<210> SEQ ID NO 1
<211> LENGTH: 678
<212> TYPE: DNA
<213> ORGANISM: Discosoma

<400> SEQUENCE: 1

```
atgaggtctt ccaagaatgt tatcaaggag ttcatgaggt ttaaggttcg catggaagga      60
acggtcaatg ggcacgagtt tgaaatagaa ggcgaaggag aggggaggcc atacgaaggc     120
cacaataccg taaagcttaa ggtaaccaag ggggacctt tgccatttgc ttgggatatt      180
ttgtcaccac aatttcagta tggaagcaag gtatatgtca agcaccctgc cgacatacca     240
gactataaaa agctgtcatt tcctgaagga tttaaatggg aaagggtcat gaactttgaa     300
gacggtggcg tcgttactgt aacccaggat ccagtttgc aggatggctg tttcatctac      360
aaggtcaagt tcattggcgt gaactttcct tccgatggac ctgttatgca aagaagaca      420
atgggctggg aagccagcac tgagcgtttg tatcctcgtg atggcgtgtt gaaggagag       480
attcataagg ctctgaagct gaaagacggt ggtcattacc tagttgaatt caaaagtatt     540
tacatggcaa agaagcctgt gcagctacca gggtactact atgttgactc caaactggat     600
ataacaagcc acaacgaaga ctatacaatc gttgagcagt atgaaagaac cgagggacgc     660
caccatctgt tcctttaa                                                    678
```

<210> SEQ ID NO 2
<211> LENGTH: 225
<212> TYPE: PRT
<213> ORGANISM: Discosoma

<400> SEQUENCE: 2

```
Met Arg Ser Ser Lys Asn Val Ile Lys Glu Phe Met Arg Phe Lys Val
1               5                   10                  15

Arg Met Glu Gly Thr Val Asn Gly His Glu Phe Glu Ile Glu Gly Glu
            20                  25                  30

Gly Glu Gly Arg Pro Tyr Glu Gly His Asn Thr Val Lys Leu Lys Val
        35                  40                  45

Thr Lys Gly Gly Pro Leu Pro Phe Ala Trp Asp Ile Leu Ser Pro Gln
    50                  55                  60

Phe Gln Tyr Gly Ser Lys Val Tyr Val Lys His Pro Ala Asp Ile Pro
65                  70                  75                  80

Asp Tyr Lys Lys Leu Ser Phe Pro Glu Gly Phe Lys Trp Glu Arg Val
                85                  90                  95

Met Asn Phe Glu Asp Gly Gly Val Val Thr Val Thr Gln Asp Ser Ser
            100                 105                 110

Leu Gln Asp Gly Cys Phe Ile Tyr Lys Val Lys Phe Ile Gly Val Asn
        115                 120                 125

Phe Pro Ser Asp Gly Pro Val Met Gln Lys Lys Thr Met Gly Trp Glu
    130                 135                 140
```

```
Ala Ser Thr Glu Arg Leu Tyr Pro Arg Asp Gly Val Leu Lys Gly Glu
145                 150                 155                 160

Ile His Lys Ala Leu Lys Leu Lys Asp Gly Gly His Tyr Leu Val Glu
                165                 170                 175

Phe Lys Ser Ile Tyr Met Ala Lys Lys Pro Val Gln Leu Pro Gly Tyr
                180                 185                 190

Tyr Tyr Val Asp Ser Lys Leu Asp Ile Thr Ser His Asn Glu Asp Tyr
            195                 200                 205

Thr Ile Val Glu Gln Tyr Glu Arg Thr Glu Gly Arg His His Leu Phe
        210                 215                 220

Leu
225

<210> SEQ ID NO 3
<211> LENGTH: 704
<212> TYPE: DNA
<213> ORGANISM: Discosoma

<400> SEQUENCE: 3
ggatccacta gtcgccacca tggcctcctc cgaggacgtc atcaaggagt tcatgcgctt      60
caaggtgcgc atggagggct ccgtgaacgg ccacgagttc gagatcgagg gcgagggcga     120
gggccgcccc tacgagggca cccagaccgc caagctgaag gtgaccaagg gcggcccct      180 gcccttcgcc tgggacatcc tgtccccca gttccagtac ggctccaagg tgtacgtgaa      240
gcaccccgcc gacatccccg actacaagaa gctgtccttc cccgagggct caagtggga      300 gcgcgtgatg aacttcgagg acggcggcgt ggtgaccgtg acccaggact cctccctgca     360
ggacggctcc ttcatctaca aggtgaagtt catcggcgtg aacttcccct ccgacggccc     420
cgtaatgcag aagaagacta tgggctggga ggcctccacc gagcgcctgt accccgcga     480 cggcgtgctg aagggcgaga tccacaaggc cctgaagctg aaggacggcg ccactacct     540 ggtggagttc aagtccatct acatggccaa gaagcccgtg cagctgcccg gctactacta     600
cgtggactcc aagctggaca tcacctccca caacgaggac tacaccatcg tggagcagta     660
cgagcgcgcc gagggccgcc accacctgtt cctgtagcgg ccgc                      704
```

US 8,664,471 B2

RAPIDLY MATURING FLUORESCENT PROTEINS AND METHODS FOR USING THE SAME

ACKNOWLEDGEMENT OF GOVERNMENT SUPPORT

The Government may own rights in the present invention pursuant to Grant Number 9875939 from the National Science Foundation.

CROSS-REFERENCE TO RELATED APPLICATIONS

This application is a continuation of application serial no. PCT/US02/40539 filed on Dec. 18, 2002; which application, pursuant to 35 U.S.C. §119 (e), claims priority to the filing date of U.S. Provisional Patent Application Ser. No. 60/341, 723 filed Dec. 19, 2001; the disclosures of which are herein incorporated by reference.

INTRODUCTION

1. Field of the Invention

The field of this invention is fluorescent proteins.

2. Background of the Invention

Labeling is a tool for marking a protein, cell, or organism of interest and plays a prominent role in many biochemistry, molecular biology and medical diagnostic applications. A variety of different labels have been developed, including radiolabels, chromolabels, fluorescent labels, chemiluminescent labels, etc. However, there is continued interest in the development of new labels. Of particular interest is the development of new protein labels, including chromo- and/or fluorescent protein labels.

An important new class of fluorescent proteins that have recently been developed are the Reef Coral Fluorescent Proteins, as described in Matz, M. V., et al. (1999) Nature Biotechnol., 17:969-973. While these fluorescent proteins exhibit many positive attributes, there is intense interest in the development of versions of this important new class of fluorescent proteins that exhibit additional desirable features, e.g., fast maturation. The present invention satisfies this need.

Relevant Literature

U.S. patents of interest include: U.S. Pat. Nos. 6,066,476; 6,020,192; 5,985,577; 5,976,796; 5,968,750; 5,968,738; 5,958,713; 5,919,445; 5,874,304; and 5,491,084. International Patent Publications of interest include: WO 00/46233; WO 99/49019; and DE 197 18 640 A. Also of interest are: Anderluh et al., Biochemical and Biophysical Research Communications (1996) 220:437-442; Dove et al., Biological Bulletin (1995) 189:288-297; Fradkov et al., FEBS Lett. (2000) 479(3):127-30; Gurskaya et al., FEBS Lett., (2001) 507(1):16-20; Gurskaya et al., BMC Biochem. (2001) 2:6; Lukyanov, K., et al (2000) J Biol Chemistry 275(34):25879-25882; Macek et al., Eur. J. Biochem. (1995) 234:329-335; Martynov et al., J Biol Chem. (2001) 276:21012-6; Matz, M. V., et al. (1999) Nature Biotechnol., 17:969-973; Terskikh et al., Science (2000) 290:1585-8; Tsien, Annual Rev. of Biochemistry (1998) 67:509-544; Tsien, Nat. Biotech. (1999) 17:956-957; Ward et al., J. Biol. Chem. (1979) 254:781-788; Wiedermann et al., Jarhrestagung der Deutschen Gesellschact fur Tropenokologie-gto. Ulm. 17-19.02.1999. Poster P-4.20; Yarbrough et al., Proc Natl Acad Sci U S A (2001) 98:462-7.

SUMMARY OF THE INVENTION

Nucleic acid compositions encoding rapidly maturing fluorescent proteins, as well as non-aggregating versions thereof (and mutants thereof) and the proteins encoded by the same, are provided. The proteins of interest are proteins that are fluorescent, where this feature arises from the interaction of two or more residues of the protein. The subject proteins are further characterized in that, in certain embodiments, they are found in or are mutants of wild-type proteins that are obtained from either non-bioluminescent Cnidarian, e.g., Anthozoan, species or are obtained from Anthozoan non-Pennatulacean (sea pen) species. In certain embodiments, the subject proteins are mutants of the wild type Discosoma sp. "red" fluorescent protein sold commercially as "DsRed". Also of interest are proteins that are substantially similar to, or mutants of, the above specific proteins. Also provided are fragments of the nucleic acids and the peptides encoded thereby, as well as antibodies to the subject proteins and transgenic cells and organisms. The subject protein and nucleic acid compositions find use in a variety of different applications. Finally, kits for use in such applications, e.g., that include the subject nucleic acid compositions, are provided.

DEFINITIONS

Figure 1:
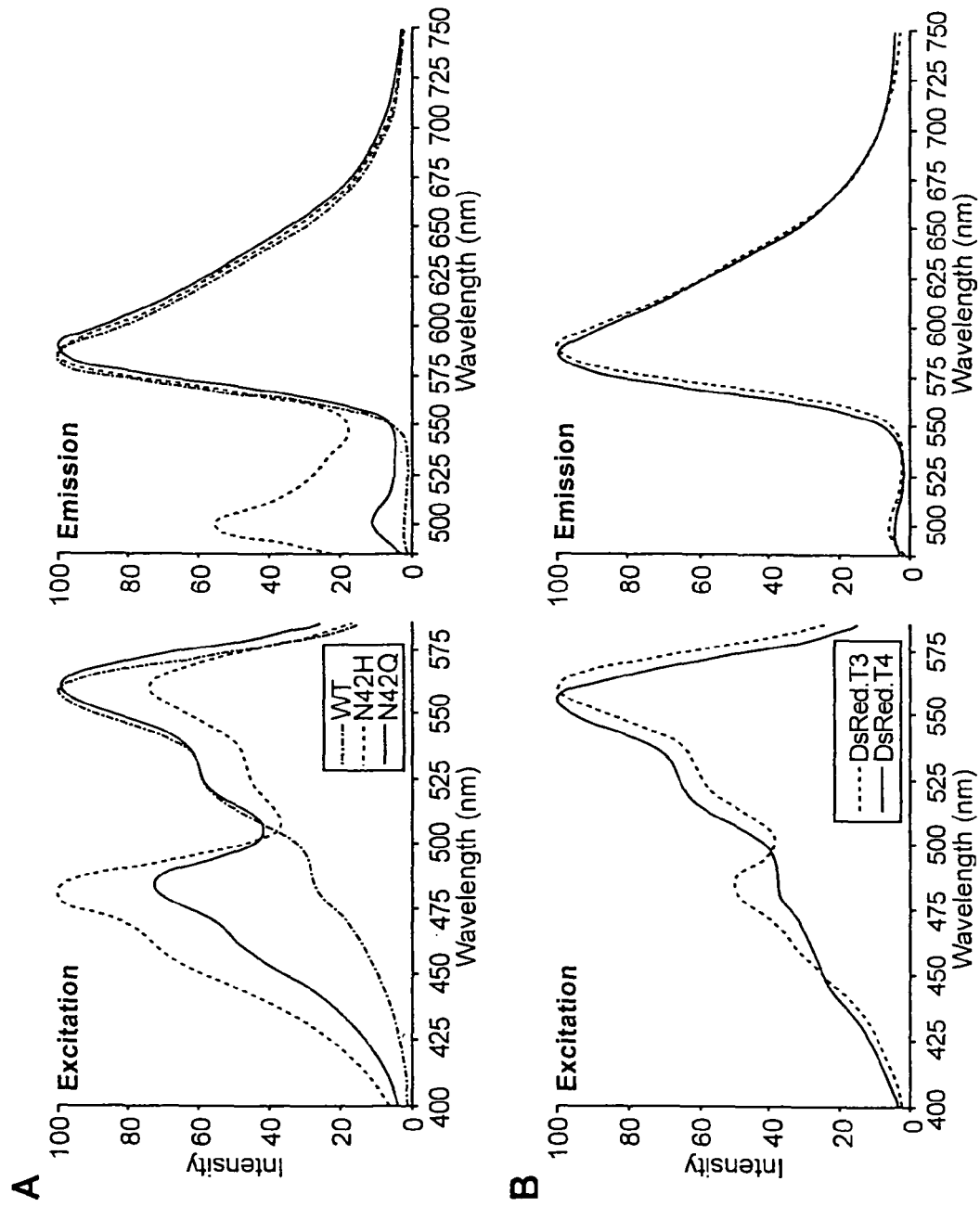
FIG. 1. Normalized excitation and emission spectra of representative DsRed variants. (A) Mutating residue N42 alters the spectral properties of DsRed. Spectra are shown for DsRed1 and the N42H and N42Q variants. All three proteins were fully mature. (B) Spectra of the optimized DsRed.T3 and DsRed.T4 variants.

In accordance with the present invention there may be employed conventional molecular biology, microbiology, and recombinant DNA techniques within the skill of the art. Such techniques are explained fully in the literature. See, e.g., Maniatis, Fritsch & Sambrook, "Molecular Cloning: A Laboratory Manual (1982); "DNA Cloning: A Practical Approach," Volumes I and II (D. N. Glover ed. 1985); "Oligonucleotide Synthesis" (M. J. Gait ed. 1984); "Nucleic Acid Hybridization" (B. D. Hames & S. J. Higgins eds. (1985)); "Transcription and Translation" (B. D. Hames & S. J. Higgins eds. (1984)); "Animal Cell Culture" (R. I. Freshney, ed. (1986)); "Immobilized Cells and Enzymes" (IRL Press, (1986)); B. Perbal, "A Practical Guide To Molecular Cloning" (1984).

A "vector" is a replicon, such as plasmid, phage or cosmid, to which another DNA segment may be attached so as to bring about the replication of the attached segment.

A "DNA molecule" refers to the polymeric form of deoxyribonucleotides (adenine, guanine, thymine, or cytosine) in either single stranded form or a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes.

A DNA "coding sequence" is a DNA sequence which is transcribed and translated into a polypeptide in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and synthetic DNA sequences. A polyadenylation signal and transcription termination sequence may be located 3' to the coding sequence.

As used herein, the term "hybridization" refers to the process of association of two nucleic acid strands to form an antiparallel duplex stabilized by means of hydrogen bonding between residues of the opposite nucleic acid strands.

The term "oligonucleotide" refers to a short (under 100 bases in length) nucleic acid molecule.

"DNA regulatory sequences", as used herein, are transcriptional and translational control sequences, such as promoters, enhancers, polyadenylation signals, terminators, and the like, that provide for and/or regulate expression of a coding sequence in a host cell.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site, as well as protein binding domains responsible for the binding of RNA polymerase. Eukaryotic promoters will often, but not always, contain "TATA" boxes and "CAT" boxes. Various promoters, including inducible promoters, may be used to drive the various vectors of the present invention.

As used herein, the terms "restriction endonucleases" and "restriction enzymes" refer to bacterial enzymes, each of which cut double-stranded DNA at or near a specific nucleotide sequence.

A cell has been "transformed" or "transfected" by exogenous or heterologous DNA when such DNA has been introduced inside the cell. The transforming DNA may or may not be integrated (covalently linked) into the genome of the cell. In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA. A "clone" is a population of cells derived from a single cell or common ancestor by mitosis. A "cell line" is a clone of a primary cell that is capable of stable growth in vitro for many generations.

A "heterologous" region of the DNA construct is an identifiable segment of DNA within a larger DNA molecule that is not found in association with the larger molecule in nature. Thus, when the heterologous region encodes a mammalian gene, the gene will usually be flanked by DNA that does not flank the mammalian genomic DNA in the genome of the source organism. In another example, heterologous DNA includes coding sequence in a construct where portions of genes from two different sources have been brought together so as to produce a fusion protein product. Allelic variations or naturally-occurring mutational events do not give rise to a heterologous region of DNA as defined herein.

As used herein, the term "reporter gene" refers to a coding sequence attached to heterologous promoter or enhancer elements and whose product may be assayed easily and quantifiably when the construct is introduced into tissues or cells.

The amino acids described herein are preferred to be in the "L" isomeric form. The amino acid sequences are given in one-letter code (A: alanine; C: cysteine; D: aspartic acid; E: glutamic acid; F: phenylalanine; G: glycine; H: histidine; I: isoleucine; K: lysine; L: leucine; M: methionine; N: asparagine; P: proline; Q: glutamine; R: arginine; S: serine; T: threonine; V: valine; W: tryptophan; Y: tyrosine; X: any residue). NH$_2$ refers to the free amino group present at the amino terminus of a polypeptide. COOH refers to the free carboxy group present at the carboxy terminus of a polypeptide. In keeping with standard polypeptide nomenclature, *J Biol. Chem.*, 243 (1969), 3552-59 is used.

The term "immunologically active" defines the capability of the natural, recombinant or synthetic chromo/fluorescent protein, or any oligopeptide thereof, to induce a specific immune response in appropriate animals or cells and to bind with specific antibodies. As used herein, "antigenic amino acid sequence" means an amino acid sequence that, either alone or in association with a carrier molecule, can elicit an antibody response in a mammal. The term "specific binding," in the context of antibody binding to an antigen, is a term well understood in the art and refers to binding of an antibody to the antigen to which the antibody was raised, but not other, unrelated antigens.

As used herein the term "isolated" is meant to describe a polynucleotide, a polypeptide, an antibody, or a host cell that is in an environment different from that in which the polynucleotide, the polypeptide, the antibody, or the host cell naturally occurs.

Bioluminescence (BL) is defined as emission of light by living organisms that is well visible in the dark and affects visual behavior of animals (See e.g., Harvey, E. N. (1952). *Bioluminescence*. New York: Academic Press; Hastings, J. W. (1995). Bioluminescence. In: *Cell Physiology* (ed. by N. Speralakis). pp. 651-681. New York: Academic Press.; Wilson, T. and Hastings, J. W. (1998). Bioluminescence. *Annu Rev Cell Dev Biol* 14, 197-230.). Bioluminescence does not include so-called ultra-weak light emission, which can be detected in virtually all living structures using sensitive luminometric equipment (Murphy, M. E. and Sies, H. (1990). Visible-range low-level chemiluminescence in biological systems. *Meth.Enzymol.* 186, 595-610; Radotic, K, Radenovic, C, Jeremic, M. (1998.) Spontaneous ultra-weak bioluminescence in plants: origin, mechanisms and properties. *Gen Physiol Biophys* 17, 289-308), and from weak light emission which most probably does not play any ecological role, such as the glowing of bamboo growth cone (Totsune, H., Nakano, M., Inaba, H. (1993). Chemiluminescence from bamboo shoot cut. *Biochem. Biophys. Res Comm.* 194, 1025-1029) or emission of light during fertilization of animal eggs (Klebanoff, S. J., Froeder, C. A., Eddy, E. M., Shapiro, B. M. (1979). Metabolic similarities between fertilization and phagocytosis. Conservation of peroxidatic mechanism. *J. Exp. Med.* 149, 938-953; Schomer, B. and Epel, D. (1998). Redox changes during fertilization and maturation of marine invertebrate eggs. *Dev Biol* 203, 1-11).

DESCRIPTION OF THE SPECIFIC EMBODIMENTS

Nucleic acid compositions encoding rapidly maturing fluorescent proteins, as well as non-aggregating versions thereof (and mutants thereof) and the proteins encoded the same, are provided. The proteins of interest are proteins that are fluorescent, where this feature arises from the interaction of two or more residues of the protein. The subject proteins are further characterized in that, in certain embodiments, they are mutants of wild-type proteins that are obtained either from non-bioluminescent *Cnidarian*, e.g., *Anthozoan*, species or are obtained from *Anthozoan* non-*Pennatulacean* (sea pen) species. In certain embodiments, the subject proteins are mutants of wild type *Discosoma* sp. "red" fluorescent protein. Also of interest are proteins that are substantially similar to, or mutants of, the above specific proteins. Also provided are fragments of the nucleic acids and the peptides encoded thereby, as well as antibodies to the subject proteins and transgenic cells and organisms. The subject protein and nucleic acid compositions find use in a variety of different applications. Finally, kits for use in such applications, e.g., that include the subject nucleic acid compositions, are provided.

Before the subject invention is described further, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

In this specification and the appended claims, the singular forms "a," "an" and "the" include plural reference unless the context clearly dictates otherwise. Unless defined otherwise, all technical and scientific terms used herein have the same meaning as commonly understood to one of ordinary skill in the art to which this invention belongs.

Where a range of values is provided, it is understood that each intervening value, to the tenth of the unit of the lower limit unless the context clearly dictates otherwise, between the upper and lower limit of that range, and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

All publications mentioned herein are incorporated herein by reference for the purpose of describing and disclosing the cell lines, vectors, methodologies and other invention components that are described in the publications that might be used in connection with the presently described invention.

In further describing the subject invention, the subject nucleic acid compositions will be described first, followed by a discussion of the subject protein compositions, antibody compositions and transgenic cells/organisms. Next a review of representative methods in which the subject proteins find use is provided.

Nucleic Acid Compositions

As summarized above, the subject invention provides nucleic acid compositions encoding rapidly maturing chromo/fluoroproteins and mutants thereof, as well as fragments and homologues of these proteins. By rapidly maturing chromo/fluorescent protein is meant a protein that is colored and/or fluorescent, e.g., it may exhibit low, medium or high fluorescence upon irradiation with light of an excitation wavelength. Furthermore, since the protein is rapidly maturing, it achieves its final chromo/fluorescent properties in less than about 72 hours, sometimes less than 48 hours, and sometimes less than 24 hours. In certain embodiments, the protein may mature in a period of less than 20 hours, e.g., 18 hours, 16 hours, 14 hours, 12 hours, 10 hours, 8 hours, etc.

In any event, the subject proteins of interest are those in which the colored characteristic, i.e., the chromo and/or fluorescent characteristic, is one that arises from the interaction of two or more residues of the protein, and not from a single residue, more specifically a single side chain of a single residue, of the protein. As such, fluorescent proteins of the subject invention do not include proteins that exhibit fluorescence only from residues that act by themselves as intrinsic fluors, i.e., tryptophan, tyrosine and phenylalanine. As such, the fluorescent proteins of the subject invention are fluorescent proteins whose fluorescence arises from some structure in the protein that is other than the above-specified single residues, e.g., it arises from an interaction of two or more residues.

By nucleic acid composition is meant a composition comprising a sequence of DNA having an open reading frame that encodes a chromo/fluoro polypeptide of the subject invention, i.e., a chromo/fluoroprotein gene, and is capable, under appropriate conditions, of being expressed as a chromo/fluoro protein according to the subject invention. Also encompassed in this term are nucleic acids that are homologous, substantially similar or identical to the nucleic acids of the present invention. Thus, the subject invention provides genes and coding sequences thereof encoding the proteins of the subject invention, as well as homologs thereof. The subject nucleic acids, when naturally occurring, are present in other than their natural environment, e.g., they are isolated, present in enriched amounts, etc., from their naturally occurring environment, e.g., the organism from which they are obtained.

The nucleic acids are further characterized in that, when they encode proteins that are either from, or are mutants of proteins that are from: (1) non-bioluminescent species, often non-bioluminescent *Cnidarian* species, e.g., non-bioluminescent *Anthozoan* species; or (2) from *Anthozoan* species that are not *Pennatulacean* species, i.e., that are not sea pens. As such, the nucleic acids may encode proteins that are from, or are mutants of proteins that are from, bioluminescent *Anthozoan* species, so long as these species are not *Pennatulacean* species, e.g., that are not *Renillan* or *Ptilosarcan* species. Of particular interest in certain embodiments are rapidly maturing mutants of the following specific wild type proteins (or mutants thereof): (1) amFP485, cFP484, zFP506, zFP540, drFP585, dsFP484, asFP600, dgFP512, dmFP592, as disclosed in application Ser. No. 10/006,922, the disclosure of which is herein incorporated by reference; (2) hcFP640, as disclosed in application Ser. No. 09/976,673, the disclosure of which is herein incorporated by reference; (3) CgCP, as disclosed in application Ser. No. 60/255,533, the disclosure of which is herein incorporated by reference; and (4) hcriGFP, zoanRFP, scubGFP1, scubGFP2, rfloRFP, rfloGFP, mcavRFP, mcavGFP, cgigGFP, afraGFP, rfloGFP2, mcavGFP2, mannFP, as disclosed in application Ser. No. 60/332,980, the dislcosure of which is herein incorporated by reference.

In certain embodiments, the proteins encoded by the subject nucleic acids are mutants of wild type *Discosoma* sp. "red" fluorescent protein (drFP585), where the nucleic acid coding sequence and the amino acid sequence of this protein are disclosed in application Ser. No. 10/006,922, the disclosure of which is herein incorporated by reference. Wild-Type DsRED is encoded by a nucleic acid having a sequence:

```
                                             (SEQ ID NO: 01)
ATGAGGTCTTCCAAGAATGTTATCAAGGAGTTCATGAGGTTTAAGGTTCG

CATGGAAGGAACGGTCAATGGGCACGAGTTTGAAATAGAAGGCGAAGGAG

AGGGGAGGCCATACGAAGGCCACAATACCGTAAAGCTTAAGGTAACCAAG

GGGGGACCTTTGCCATTTGCTTGGGATATTTTGTCACCACAATTTCAGTA

TGGAAGCAAGGTATATGTCAAGCACCCTGCCGACATACCAGACTATAAAA

AGCTGTCATTTCCTGAAGGATTTAAATGGGAAAGGGTCATGAACTTTGAA

GACGGTGGCGTCGTTACTGTAACCCAGGATTCCAGTTTGCAGGATGGCTG

TTTCATCTACAAGGTCAAGTTCATTGGCGTGAACTTTCCTTCCGATGGAC

CTGTTATGCAAAAGAAGACAATGGGCTGGGAAGCCAGCACTGAGCGTTTG

TATCCTCGTGATGGCGTGTTGAAAGGAGAGATTCATAAGGCTCTGAAGCT

GAAAGACGGTGGTCATTACCTAGTTGAATTCAAAAGTATTTACATGGCAA

AGAAGCCTGTGCAGCTACCAGGGTACTACTATGTTGACTCCAAACTGGAT

ATAACAAGCCACAACGAAGACTATACAATCGTTGAGCAGTATGAAAGAAC

CGAGGGACGCCACCATCTGTTCCTTTAA
``` and has the amino acid sequence:

```
                                             (SEQ ID NO: 02)
MRSSKNVIKEFMRFKVRMEGTVNGHEFEIEGEGEGRPYEGHNTVKLKVTK

GGPLPFAWDILSPQFQYGSKVYVKHPADIPDYKKLSFPEGFKWERVMNFE

DGGVVTVTQDSSLQDGCFIYKVKFIGVNFPSDGPVMQKKTMGWEASTERL

YPRDGVLKGEIHKALKLKDGGHYLVEFKSIYMAKKPVQLPGYYYVDSKLD

ITSHNEDYTIVEQYERTEGRHHLFL
```

Representative rapidly maturing mutants of "DsRed" include, but are not limited to: point mutations at position 42 relative to the start residue, e.g., N42H, N42Q, etc.; point mutations at position 41 relative to the start residue, e.g., H41L, H41T, etc.; point mutations at position 44 relative to the start residue, e.g., V44A, etc.; point mutations at position 21 relative to the start residue, e.g., T21S, etc.; and the like.

One representative nucleic acid of interest that encodes the DsRed.T1 mutant described in greater detail below includes coding sequence found in the following sequence:

```
                                             (SEQ ID NO: 03)
GGATCCACTAGTCGCCACCATGGCCTCCTCCGAGGACGTCATCAAGGAGT

TCATGCGCTTCAAGGTGCGCATGGAGGGCTCCGTGAACGGCCACGAGTTC

GAGATCGAGGGCGAGGGCGAGGGCCGCCCCTACGAGGGCACCCAGACCGC

CAAGCTGAAGGTGACCAAGGGCGGCCCCCTGCCCTTCGCCTGGGACATCC

TGTCCCCCCAGTTCCAGTACGGCTCCAAGGTGTACGTGAAGCACCCCGCC

GACATCCCCGACTACAAGXAGCTGTCCTTCCCCGAGGGCTTCAAGTGGGA

GCGCGTGATGAACTTCGAGGACGGCGGCGTGGTGACCGTGACCCAGGACT

CCTCCCTGCAGGACGGCTCCTTCATCTACAAGGTGAAGTTCATCGGCGTG

AACTTCCCCTCCGACGGCCCCGTAATGCAGAAGAAGACTATGGGCTGGGA

GGCCTCCACCGAGCGCCTGTACCCCCGCGACGGCGTGCTGAAGGGCGAGA

TCCACAAGGCCCTGAAGCTGAAGGACGGCGGCCACTACCTGGTGGAGTTC

AAGTCCATCTACATGGCCAAGAAGCCCGTGCAGCTGCCCGGCTACTACTA
```

-continued
CGTGGACTCCAAGCTGGACATCACCTCCCACAACGAGGACTACACCATCG

TGGAGCAGTACGAGCGCGCCGAGGGCCGCCACCACCTGTTCCTGTAGCGG

CCGC where the bolded/underlined ATG codon is the start codon and the bold/underlined TAG is the stop codon.

In addition to the above-described fast maturing DsRed mutants, fast-maturing mutants of other species as mentioned above are also of interest. Such mutants or variants have point mutations such as those described above in analogous or corresponding positions of their sequence with respect to the specific positions identified in the above representative DsRed mutants. Analogous or corresponding sequence positions to make point mutations in a given protein are readily determining by aligning the enclosed specific DsRed mutants and the sequences of the wildtype protein from the species of interest with *Aquoria victoria* green fluorescent protein, using the protocol described in, and as illustrated in FIG. 1 of, Matz et al., Nature Biotechnology (1999) 969-973. Specific representative fast-maturing mutants of other species include, but are not limited to (where the following point positions are numbered according to the "GFP" numbering protocol illustrated in FIG. 1 of Matz et al., supra): (1) fast maturing mutants of dsFP483 having one or more point mutations selected from N42, e.g., Q or H, V44, e.g., A, T21, e.g., S; fast maturing mutants of zFP506 having one or more point mutations selected from K41, e.g., L or T, I44, e.g., A, C21, e.g., S; fast maturing mutants of aFP538 having one or more point mutations selected from K41, e.g., L or T, I44, e.g., A, C21, e.g., S; fast maturing mutants of amFP483 having one or more point mutations selected from C21, e.g., S; and fast maturing mutants of cFP484 having one or more point mutations selected from N21, e.g., S, L44, e.g. A; etc.

In addition to the above-described specific nucleic acid compositions, also of interest are homologues of the above-sequences. With respect to homologues of the subject nucleic acids, the source of homologous genes may be any species of plant or animal or the sequence may be wholly or partially synthetic. In certain embodiments, sequence similarity between homologues is at least about 20%, sometimes at least about 25%, and may be 30%, 35%, 40%, 50%, 60%, 70% or higher, including 75%, 80%, 85%, 90% and 95% or higher. Sequence similarity is calculated based on a reference sequence, which may be a subset of a larger sequence, such as a conserved motif, coding region, flanking region, etc. A reference sequence will usually be at least about 18 nt long, more usually at least about 30 nt long, and may extend to the complete sequence that is being compared. Algorithms for sequence analysis are known in the art, such as BLAST, described in Altschul et al. (1990), *J. Mol. Biol.* 215:403-10 (using default settings, i.e. parameters w=4 and T=17). The sequences provided herein are essential for recognizing related and homologous nucleic acids in database searches.

Of particular interest in certain embodiments are nucleic acids of substantially the same length as the nucleic acid identified as SEQ ID NO: 01 or 02, where by substantially the same length is meant that any difference in length does not exceed about 20 number %, usually does not exceed about 10 number % and more usually does not exceed about 5 number %; and have sequence identity to any of these sequences of at least about 90%, usually at least about 95% and more usually at least about 99% over the entire length of the nucleic acid. In many embodiments, the nucleic acids have a sequence that is substantially similar (i.e., the same as) or identical to the sequence of SEQ ID NO: 01 or 02. By substantially similar is meant that sequence identity will generally be at least about 60%, usually at least about 75% and often at least about 80, 85, 90, or even 95%.

Also provided are nucleic acids that encode the proteins encoded by the above-described nucleic acids, but differ in sequence from the above-described nucleic acids due to the degeneracy of the genetic code.

Also provided are nucleic acids that hybridize to the above-described nucleic acid under stringent conditions. An example of stringent hybridization conditions is hybridization at 50° C. or higher and 0.1×SSC (15 mM sodium chloride/1.5 mM sodium citrate). Another example of stringent hybridization conditions is overnight incubation at 42° C. in a solution: 50% formamide, 5×SSC (150 mM NaCl, 15 mM trisodium citrate), 50 mM sodium phosphate (pH7.6), 5× Denhardt's solution, 10% dextran sulfate, and 20 µg/ml denatured, sheared salmon sperm DNA, followed by washing the filters in 0.1×SSC at about 65° C. Stringent hybridization conditions are hybridization conditions that are at least as stringent as the above representative conditions, where conditions are considered to be at least as stringent if they are at least about 80% as stringent, typically at least about 90% as stringent as the above specific stringent conditions. Other stringent hybridization conditions are known in the art and may also be employed to identify nucleic acids of this particular embodiment of the invention.

Nucleic acids encoding mutants of the proteins of the invention are also provided. Mutant nucleic acids can be generated by random mutagenesis or targeted mutagenesis, using well-known techniques that are routine in the art. In some embodiments, chromo- or fluorescent proteins encoded by nucleic acids encoding homologues or mutants have the same fluorescent properties as the wild-type fluorescent protein. In other embodiments, homologue or mutant nucleic acids encode chromo- or fluorescent proteins with altered spectral properties, as described in more detail herein.

One category of mutant that is of particular interest is the non-aggregating mutant. In many embodiments, the non-aggregating mutant differs from the wild type sequence by a mutation in the N-terminus that modulates the charges appearing on side groups of the N-terminus residues, e.g., to reverse or neutralize the charge, in a manner sufficient to produce a non-aggregating mutant of the naturally occurring protein or mutant, where a particular protein is considered to be non-aggregating if it is determined be non-aggregating using the assay reported in U.S. patent application Ser. No. 10/081,864, the disclosure of which is herein incorporated by reference, and published in PCT publication No. WO 02/068459.

In some embodiments, nucleic acids of this embodiment encode non-aggregating polypeptides that exhibit reduced aggregation in vivo. "Reduced aggregation in vivo" refers to reduced aggregation in a cell. In some embodiments, the non-aggregating polypeptide shows less than about 90%, less than about 80%, less than about 70%, less than about 60%, less than about 50%, less than about 40%, less than about 30%, less than about 25%, less than about 20%, less than about 15%, less than about 10%, or less than about 5% of the aggregation shown by its corresponding aggregating analogue under the same in vivo conditions, e.g., in another eukaryotic cell from the same cell line, in an identical prokaryotic cell, or in a eukaryotic cell or cell population of the same cell type. In general, less than about 60%, less than about 50%, less than about 40%, less than about 30%, less than about 20%, less than about 10%, or less than about 5%, of the subject non-aggregating polypeptide present in a cell or a cell population is aggregated.

Methods of measuring the degree of aggregation are known in the art; any known method can be used to determine whether a given mutant shows a reduction in aggregation compared to corresponding aggregating analogue, e.g., when compared to a corresponding aggregating wild type polypeptide. Such methods include, but are not limited to, "pseudo-native" protein gel electrophoresis; gel filtration; ultracentrifugation; circular dichroism; and light scattering. Aggregation can be measured by light scattering. For non-aggregated proteins, the ratio of absorption at a shorter wavelength to the absorption at a longer wavelength is close to zero. In some embodiments, the ratio of absorption at 400 nm to the absorption at 566 nm of a non-aggregating polypeptide is in the range of from about 0.01 to about 0.1, from about 0.015 to about 0.09, from about 0.02 to about 0.08, from about 0.025 to about 0.07, or from about 0.03 to about 0.06.

In many embodiments, the nucleic acids encode non-aggregating rapidly maturing polypeptides that have amino acid sequences that differ from their corresponding wild type sequences by a mutation in the N-terminus that modulates the charges appearing on side groups of the N-terminus residues, e.g., to reverse or neutralize the charge, in a manner sufficient to produce a non-aggregating mutant of the naturally occurring protein or aggregating mutant thereof. More specifically, basic residues located near the N-termini of the proteins are substituted, e.g., Lys and Arg residues close to the N-terminus are substituted with negatively charged or neutral residues. By N-terminus is meant within about 50 residues from the N-terminus, often within about 25 residues of the N-terminus and more often within about 15 residues of the N-terminus, where in many embodiments, residue modifications occur within about 10 residues of the N-terminus. Specific residues of interest in many embodiments include: 2, 3, 4, 5, 6, 7, 8, 9 and 10.

Where the protein encoded by the nucleic acid is a DsRed mutant, as described above, specific non-aggregating point mutations of interest include, but are not limited to: mutations at position 2, e.g., R2H, R2L, R2A, etc.; mutations at position 5, e.g., K5E, K5Q, K5M, etc.; mutations at position 6, e.g., N6D, etc.; and the like.

Another category of mutant of particular interest is the modulated oligomerization mutant. A mutant is considered to be a modulated oligomerization mutant if its oligomerization properties are different as compared to the wild type protein. For example, if a particular mutant oligomerizes to a greater or lesser extent than the wild type, it is considered to be an oligomerization mutant. Of particular interest are oligomerization mutants that do not oligomerize, i.e., are monomers under physiological (e.g., intracellular) conditions, or oligomerize to a lesser extent that the wild type, e.g., are dimers or trimers under intracellular conditions. As such, of particular interest are nucleic acids that encode monomeric versions of the subject rapidly maturing proteins. One representative monomeric variant of the rapidly maturing DsRed proteins described herein is the mutant named mRFP1 (monomeric red fluorescent protein) and described in Campbell et al., Proc. Natl. Acad. Sci. USA. 2002 June 11; 99 (12): 7877-7882. This specific mutant contains a total of 33 mutations relative to DsRed of which 13 are internal to the β-barrel (N42Q, V44A, V71A, K83L, F124L, L150M, K163M, V175A, F177V, S179T, V195T, S197I, and T217A); three are the aggregation-reducing mutations from T1 (R2A, K5E, and N6D), three are AB interface mutations (I125R, V127T, and I180T), ten are AC interface mutations (R153E, H162K, A164R, L174D, Y192A, Y194K, H222S, L223T, F224G, and L225A), and four are additional beneficial mutations (T21S, H41T, C117E, and V156A). The nucleic acid and amino acid sequences for this protein having been deposited with GEN-BANK and assigned an accession no. of AF506027.

Nucleic acids of the subject invention may be cDNA or genomic DNA or a fragment thereof. In certain embodiments, the nucleic acids of the subject invention include one or more of the open reading frames encoding specific fluorescent proteins and polypeptides, and introns, as well as adjacent 5' and 3' non-coding nucleotide sequences involved in the regulation of expression, up to about 20 kb beyond the coding region, but possibly further in either direction. The subject nucleic acids may be introduced into an appropriate vector for extrachromosomal maintenance or for integration into a host genome, as described in greater detail below.

The term "cDNA" as used herein is intended to include all nucleic acids that share the arrangement of sequence elements found in native mature mRNA species, where sequence elements are exons and 5' and 3' non-coding regions. Normally mRNA species have contiguous exons, with the intervening introns, when present, being removed by nuclear RNA splicing, to create a continuous open reading frame encoding the protein.

A genomic sequence of interest comprises the nucleic acid present between the initiation codon and the stop codon, as defined in the listed sequences, including all of the introns that are normally present in a native chromosome. It may further include 5' and 3' un-translated regions found in the mature mRNA. It may further include specific transcriptional and translational regulatory sequences, such as promoters, enhancers, etc., including about 1 kb, but possibly more, of flanking genomic DNA at either the 5' or 3' end of the transcribed region. The genomic DNA may be isolated as a fragment of 100 kbp or smaller; and substantially free of flanking chromosomal sequence. The genomic DNA flanking the coding region, either 3' or 5', or internal regulatory sequences as sometimes found in introns, contains sequences required for proper tissue and stage specific expression.

The nucleic acid compositions of the subject invention may encode all or a part of the subject proteins. Double or single stranded fragments may be obtained from the DNA sequence by chemically synthesizing oligonucleotides in accordance with conventional methods, by restriction enzyme digestion, by PCR amplification, etc. For the most part, DNA fragments will be of at least about 15 nt, usually at least about 18 nt or about 25 nt, and may be at least about 50 nt. In some embodiments, the subject nucleic acid molecules may be about 100 nt, about 200 nt, about 300 nt, about 400 nt, about 500 nt, about 600 nt, about 700 nt, or about 720 nt in length. The subject nucleic acids may encode fragments of the subject proteins or the full-length proteins, e.g., the subject nucleic acids may encode polypeptides of about 25 aa, about 50 aa, about 75 aa, about 100 aa, about 125 aa, about 150 aa, about 200 aa, about 210 aa, about 220 aa, about 230 aa, or about 240 aa, up to the entire protein.

The subject nucleic acids are isolated and obtained in substantial purity, generally as other than an intact chromosome. Usually, the DNA will be obtained substantially free of other nucleic acid sequences that do not include a nucleic acid of the subject invention or fragment thereof, generally being at least about 50%, usually at least about 90% pure and are typically "recombinant", i.e. flanked by one or more nucleotides with which it is not normally associated on a naturally occurring chromosome.

The subject polynucleotides (e.g., a polynucleotide having a sequence of SEQ ID NO: 01) the corresponding cDNA, the full-length gene and constructs of the subject polynucleotides are provided. These molecules can be generated synthetically by a number of different protocols known to those of skill in the art. Appropriate polynucleotide constructs are purified using standard recombinant DNA techniques as described in, for example, Sambrook et al., *Molecular Cloning: A Laboratory Manual, 2nd Ed.*, (1989) Cold Spring Harbor Press, Cold Spring Harbor, N.Y., and under current regulations described in United States Dept. of HHS, National Institute of Health (NIH) Guidelines for Recombinant DNA Research.

Also provided are nucleic acids that encode fusion proteins of the subject proteins, or fragments thereof, which are fused to a second protein, e.g., a degradation sequence, a signal peptide, etc. For example, of interest are fusions of the present proteins with rapid degradation sequences, such as those described in U.S. Pat. No. 6,306,600 (the disclosure of which is herein incorporated by reference), the degradation domain of mouse ornithine decarboxylase (MODC), which contains a PEST sequence. A representative fusion protein of this embodiment is marketed under the name "Destabilized DsRed-Express" by BD Biosciences Clontech (Palo Alto Calif.). Fusion proteins may comprise a subject polypeptide, or fragment thereof, and a non-*Anthozoan* polypeptide ("the fusion partner") fused in-frame at the N-terminus and/or C-terminus of the subject polypeptide. Fusion partners include, but are not limited to, polypeptides that can bind antibody specific to the fusion partner (e.g., epitope tags); antibodies or binding fragments thereof; polypeptides that provide a catalytic function or induce a cellular response; ligands or receptors or mimetics thereof; and the like. In such fusion proteins, the fusion partner is generally not naturally associated with the subject *Anthozoan* portion of the fusion protein, and is typically not an *Anthozoan* protein or derivative/fragment thereof, i.e., it is not found in *Anthozoan* species.

Also provided are constructs comprising the subject nucleic acids inserted into a vector, where such constructs may be used for a number of different applications, including propagation, protein production, etc. Viral and non-viral vectors may be prepared and used, including plasmids. The choice of vector will depend on the type of cell in which propagation is desired and the purpose of propagation. Certain vectors are useful for amplifying and making large amounts of the desired DNA sequence. Other vectors are suitable for expression in cells in culture. Still other vectors are suitable for transfer and expression in cells in a whole animal or person. The choice of appropriate vector is well within the skill of the art. Many such vectors are available commercially. To prepare the constructs, the partial or full-length polynucleotide is inserted into a vector typically by means of DNA ligase attachment to a cleaved restriction enzyme site in the vector. Alternatively, the desired nucleotide sequence can be inserted by homologous recombination in vivo. Typically this is accomplished by attaching regions of homology to the vector on the flanks of the desired nucleotide sequence. Regions of homology are added by ligation of oligonucleotides, or by polymerase chain reaction using primers comprising both the region of homology and a portion of the desired nucleotide sequence, for example. Representative specific vectors of interest include, but are not limited to: pCMV-DsRed-Express Vector; pDsRED-Express Vector and pDsRed-Express-1 vector; all of which are sold by BD Biosciences Clontech (Palo Alto Calif.).

Also provided are expression cassettes or systems that find use in, among other applications, the synthesis of the subject proteins. For expression, the gene product encoded by a polynucleotide of the invention is expressed in any convenient expression system, including, for example, bacterial, yeast, insect, amphibian and mammalian systems. Suitable vectors and host cells are described in U.S. Pat. No. 5,654,173. In the expression vector, a subject polynucleotide, e.g., as set forth in SEQ ID NO:01 or 02, is linked to a regulatory sequence as appropriate to obtain the desired expression properties. These regulatory sequences can include promoters (attached either at the 5' end of the sense strand or at the 3' end of the antisense strand), enhancers, terminators, operators, repressors, and inducers. The promoters can be regulated or constitutive. In some situations it may be desirable to use conditionally active promoters, such as tissue-specific or developmental stage-specific promoters. These are linked to the desired nucleotide sequence using the techniques described above for linkage to vectors. Any techniques known in the art can be used. In other words, the expression vector will provide a transcriptional and translational initiation region, which may be inducible or constitutive, where the coding region is operably linked under the transcriptional control of the transcriptional initiation region, and a transcriptional and translational termination region. These control regions may be native to the subject species from which the subject nucleic acid is obtained, or may be derived from exogenous sources.

Expression vectors generally have convenient restriction sites located near the promoter sequence to provide for the insertion of nucleic acid sequences encoding heterologous proteins. A selectable marker operative in the expression host may be present. Expression vectors may be used for, among other things, the production of fusion proteins, as described above.

Expression cassettes may be prepared comprising a transcription initiation region, the gene or fragment thereof, and a transcriptional termination region. Of particular interest is the use of sequences that allow for the expression of functional epitopes or domains, usually at least about 8 amino acids in length, more usually at least about 15 amino acids in length, to about 25 amino acids, and up to the complete open reading frame of the gene. After introduction of the DNA, the cells containing the construct may be selected by means of a selectable marker, the cells expanded and then used for expression.

The above described expression systems may be employed with prokaryotes or eukaryotes in accordance with conventional ways, depending upon the purpose for expression. For large scale production of the protein, a unicellular organism, such as *E. coli, B. subtilis, S. cerevisiae*, insect cells in combination with baculovirus vectors, or cells of a higher organism such as vertebrates, e.g. COS 7 cells, HEK 293, CHO, Xenopus Oocytes, etc., may be used as the expression host cells. In some situations, it is desirable to express the gene in eukaryotic cells, where the expressed protein will benefit from native folding and post-translational modifications. Small peptides can also be synthesized in the laboratory. Polypeptides that are subsets of the complete protein sequence may be used to identify and investigate parts of the protein important for function.

Specific expression systems of interest include bacterial, yeast, insect cell and mammalian cell derived expression systems. Representative systems from each of these categories is are provided below:

Bacteria. Expression systems in bacteria include those described in Chang et al., *Nature* (1978) 275:615; Goeddel et al., *Nature* (1979) 281:544; Goeddel et al., *Nucleic Acids Res.* (1980) 8:4057; EP 0 036,776; U.S. Pat. No. 4,551,433; DeBoer et al., *Proc. Natl. Acad. Sci.* (*USA*) (1983) 80:21-25; and Siebenlist et al., *Cell* (1980) 20:269.

Yeast. Expression systems in yeast include those described in Hinnen et al., *Proc. Natl. Acad. Sci.* (*USA*) (1978) 75:1929; Ito et al., *J. Bacteriol.* (1983) 153: 163; Kurtz et al., *Mol. Cell. Biol.* (1986) 6:142; Kunze et al., *J. Basic Microbiol.* (1985) 25:141; Gleeson et al., *J. Gen. Microbiol.* (1986) 132:3459;

Roggenkamp et al., *Mol. Gen. Genet.* (1986) 202:302; Das et al., *J. Bacteriol.* (1984) 158:1165; De Louvencourt et al., *J. Bacteriol.* (1983) 154:737; Van den Berg et al., *Bio/Technology* (1990) 8:135; Kunze et al., *J. Basic Microbiol.* (1985) 25:141; Cregg et al., *Mol. Cell. Biol.* (1985) 5:3376; U.S. Pat. Nos. 4,837,148 and 4,929,555; Beach and Nurse, *Nature* (1981) 300:706; Davidow et al., *Curr. Genet.* (1985) 10:380; Gaillardin et al., *Curr. Genet.* (1985) 10:49; Ballance et al., *Biochem. Biophys. Res. Commun.* (1983) 112:284-289; Tilburn et al., *Gene* (1983) 26:205-221; Yelton et al., *Proc. Natl. Acad. Sci.* (*USA*) (1984) 81:1470-1474; Kelly and Hynes, *EMBO J.* (1985) 4:475479; EP 0 244,234; and WO 91/00357.

Insect Cells. Expression of heterologous genes in insects is accomplished as described in U.S. Pat. No. 4,745,051; Friesen et al., "The Regulation of Baculovirus Gene Expression", in: *The Molecular Biology Of Baculoviruses* (1986) (W. Doerfler, ed.); EP 0 127,839; EP 0 155,476; and Vlak et al., *J. Gen. Virol.* (1988) 69:765-776; Miller et al., *Ann. Rev. Microbiol.* (1988) 42:177; Carbonell et al., *Gene* (1988) 73:409; Maeda et al., *Nature* (1985) 315:592-594; Lebacq-Verheyden et al., *Mol. Cell. Biol.* (1988) 8:3129; Smith et al., *Proc. Natl. Acad. Sci.* (*USA*) (1985) 82:8844; Miyajima et al., *Gene* (1987) 58:273; and Martin et al., *DNA* (1988) 7:99. Numerous baculoviral strains and variants and corresponding permissive insect host cells from hosts are described in Luckow et al., Bio/Technology (1988) 6:47-55, Miller et al., *Generic Engineering* (1986) 8:277-279, and Maeda et al., *Nature* (1985) 315:592-594.

Mammalian Cells. Mammalian expression is accomplished as described in Dijkema et al., *EMBO J.* (1985) 4:761, Gorman et al., *Proc. Natl. Acad. Sci.* (*USA*) (1982) 79:6777, Boshart et al., *Cell* (1985) 41:521 and U.S. Pat. No. 4,399,216. Other features of mammalian expression are facilitated as described in Ham and Wallace, *Meth. Enz.* (1979) 58:44, Barnes and Sato, *Anal. Biochem.* (1980) 102:255, U.S. Pat. Nos. 4,767,704, 4,657,866, 4,927,762, 4,560,655, WO 90/103430, WO 87/00195, and U.S. RE 30,985.

When any of the above host cells, or other appropriate host cells or organisms, are used to replicate and/or express the polynucleotides or nucleic acids of the invention, the resulting replicated nucleic acid, RNA, expressed protein or polypeptide, is within the scope of the invention as a product of the host cell or organism. The product is recovered by any appropriate means known in the art.

Once the gene corresponding to a selected polynucleotide is identified, its expression can be regulated in the cell to which the gene is native. For example, an endogenous gene of a cell can be regulated by an exogenous regulatory sequence inserted into the genome of the cell at location sufficient to at least enhance expressed of the gene in the cell. The regulatory sequence may be designed to integrate into the genome via homologous recombination, as disclosed in U.S. Pat. Nos. 5,641,670 and 5,733,761, the disclosures of which are herein incorporated by reference, or may be designed to integrate into the genome via non-homologous recombination, as described in WO 99/15650, the disclosure of which is herein incorporated by reference. As such, also encompassed in the subject invention is the production of the subject proteins without manipulation of the encoding nucleic acid itself, but instead through integration of a regulatory sequence into the genome of cell that already includes a gene encoding the desired protein, as described in the above incorporated patent documents.

Also provided are homologs of the subject nucleic acids. Homologs are identified by any of a number of methods. A fragment of the provided cDNA may be used as a hybridization probe against a cDNA library from the target organism of interest, where low stringency conditions are used. The probe may be a large fragment, or one or more short degenerate primers. Nucleic acids having sequence similarity are detected by hybridization under low stringency conditions, for example, at 50° C. and 6×SSC (0.9 M sodium chloride/0.09 M sodium citrate) and remain bound when subjected to washing at 55° C. in 1×SSC (0.15 M sodium chloride/0.015 M sodium citrate). Sequence identity may be determined by hybridization under stringent conditions, for example, at 50° C. or higher and 0.1×SSC (15 mM sodium chloride/1.5 mM sodium citrate). Nucleic acids having a region of substantial identity to the provided sequences, e.g. allelic variants, genetically altered versions of the gene, etc., bind to the provided sequences under stringent hybridization conditions. By using probes, particularly labeled probes of DNA sequences, one can isolate homologous or related genes.

Also of interest are promoter elements of the subject genomic sequences, where the sequence of the 5' flanking region may be utilized for promoter elements, including enhancer binding sites, e.g., that provide for regulation of expression in cells/tissues where the subject proteins gene are expressed.

Also provided are small DNA fragments of the subject nucleic acids, which fragments are useful as primers for PCR, hybridization screening probes, etc. Larger DNA fragments, i.e., greater than 100 nt are useful for production of the encoded polypeptide, as described in the previous section. For use in geometric amplification reactions, such as geometric PCR, a pair of primers will be used. The exact composition of the primer sequences is not critical to the invention, but for most applications the primers will hybridize to the subject sequence under stringent conditions, as known in the art. It is preferable to choose a pair of primers that will generate an amplification product of at least about 50 nt, preferably at least about 100 nt. Algorithms for the selection of primer sequences are generally known, and are available in commercial software packages. Amplification primers hybridize to complementary strands of DNA, and will prime towards each other.

The DNA may also be used to identify expression of the gene in a biological specimen. The manner in which one probes cells for the presence of particular nucleotide sequences, as genomic DNA or RNA, is well established in the literature. Briefly, DNA or mRNA is isolated from a cell sample. The mRNA may be amplified by RT-PCR, using reverse transcriptase to form a complementary DNA strand, followed by polymerase chain reaction amplification using primers specific for the subject DNA sequences. Alternatively, the mRNA sample is separated by gel electrophoresis, transferred to a suitable support, e.g. nitrocellulose, nylon, etc., and then probed with a fragment of the subject DNA as a probe. Other techniques, such as oligonucleotide ligation assays, in situ hybridizations, and hybridization to DNA probes arrayed on a solid chip may also find use. Detection of mRNA hybridizing to the subject sequence is indicative of Anthozoan protein gene expression in the sample.

The subject nucleic acids, including flanking promoter regions and coding regions, may be mutated in various ways known in the art to generate targeted changes in promoter strength, sequence of the encoded protein, properties of the encoded protein, including fluorescent properties of the encoded protein, etc. The DNA sequence or protein product of such a mutation will usually be substantially similar to the sequences provided herein, e.g. will differ by at least one nucleotide or amino acid, respectively, and may differ by at least two but not more than about ten nucleotides or amino acids. The sequence changes may be substitutions, insertions, deletions, or a combination thereof. Deletions may further include larger changes, such as deletions of a domain or exon, e.g. of stretches of 10, 20, 50, 75, 100, 150 or more aa residues. Techniques for in vitro mutagenesis of cloned genes are known. Examples of protocols for site specific mutagenesis may be found in Gustin et al. (1993), *Biotechniques* 14:22; Barany (1985), *Gene* 37:111-23; Colicelli et al. (1985), *Mol. Gen. Genet.* 199:537-9; and Prentki et al. (1984), *Gene* 29:303-13. Methods for site specific mutagenesis can be found in Sambrook et al., *Molecular Cloning: A Laboratory Manual*, CSH Press 1989, pp. 15.3-15.108; Weiner et al. (1993), *Gene* 126:35-41; Sayers et al. (1992), *Biotechniques* 13:592-6; Jones and Winistorfer (1992), *Biotechniques* 12:528-30; Barton et al. (1990), *Nucleic Acids Res* 18:7349-55; Marotti and Tomich (1989), *Gene Anal. Tech.* 6:67-70; and Zhu (1989), *Anal Biochem* 177:120-4. Such mutated nucleic acid derivatives may be used to study structure-function relationships of a particular chromo/ fluorescent protein, or to alter properties of the protein that affect its function or regulation.

Also of interest are humanized versions of the subject nucleic acids. As used herein, the term "humanized" refers to changes made to the nucleic acid sequence to optimize the codons for expression of the protein in human cells (Yang et al., *Nucleic Acids Research* 24 (1996), 4592-4593). See also U.S. Pat. No. 5,795,737 which describes humanization of proteins, the disclosure of which is herein incorporated by reference.

Protein/Peptide Compositions

Also provided by the subject invention are rapidly maturing chromo- and/or fluorescent proteins and mutants thereof, as well as polypeptide compositions related thereto. As the subject proteins are chromoproteins, they are colored proteins, which may be fluorescent, low or non- fluorescent. As used herein, the terms chromoprotein and fluorescent protein do not include luciferases, such as Renilla luciferase, and refer to any protein that is pigmented or colored and/or fluoresces when irradiated with light, e.g., white light or light of a specific wavelength (or narrow band of wavelengths such as an excitation wavelength). The term polypeptide composition as used herein refers to both the full-length protein, as well as portions or fragments thereof. Also included in this term are variations of the naturally occurring protein, where such variations are homologous or substantially similar to the naturally occurring protein, and mutants of the naturally occurring proteins, as described in greater detail below. The subject polypeptides are present in other than their natural environment.

In many embodiments, the excitation spectra of the subject proteins typically ranges from about 300 to 700, usually from about 350 to 650 and more usually from about 400 to 600 nm while the emission spectra of the subject proteins typically ranges from about 400 to 800, usually from about 425 to 775 and more usually from about 450 to 750 nm. The subject proteins generally have a maximum extinction coefficient that ranges from about 10,000 to 55,000 and usually from about 15,000 to 55,000. The subject proteins typically range in length from about 150 to 300 and usually from about 200 to 300 amino acid residues, and generally have a molecular weight ranging from about 15 to 35 kDa, usually from about 17.5 to 32.5 kDa.

In certain embodiments, the subject proteins are bright, where by bright is meant that the chromoproteins and their fluorescent mutants can be detected by common methods (e.g., visual screening, spectrophotometry, spectrofluorometry, fluorescent microscopy, by FACS machines, etc.) Fluorescence brightness of particular fluorescent proteins is determined by its quantum yield multiplied by maximal extinction coefficient. Brightness of chromoprotein may be expressed by its maximal extinction coefficient.

In certain embodiments, the subject proteins fold rapidly following expression in the host cell. By rapidly folding is meant that the proteins achieve their tertiary structure that gives rise to their chromo- or fluorescent quality in a short period of time. In these embodiments, the proteins fold in a period of time that generally does not exceed about 3 days, usually does not exceed about 2 days and more usually does not exceed about 1 day.

Specific proteins of interest include rapidly maturing variants of DsRed, which mature at least about 5 times more rapidly, sometimes at least about 10 times more rapidly, e.g., at least about 15 times more rapidly or faster, than the corresponding DsRed wild type protein. Exemplary proteins of this specific embodiment include those described in the experimental section, below, e.g., DsRed.T1; DsRed.T3; and DsRedT4.

Homologs or proteins (or fragments thereof) that vary in sequence from the above provided specific amino acid sequences of the subject invention are also provided. By homolog is meant a protein having at least about 10%, usually at least about 20% and more usually at least about 30%, and in many embodiments at least about 35%, usually at least about 40% and more usually at least about 60% amino acid sequence identity to the protein of the subject invention, as determined using MegAlign, DNAstar (1998) clustal algorithm as described in D. G. Higgins and P. M. Sharp, "Fast and Sensitive multiple Sequence Alignments on a Microcomputer," (1989) CABIOS, 5: 151-153. (Parameters used are ktuple 1, gap penalty 3, window, 5 and diagonals saved 5). In many embodiments, homologues of interest have much higher sequence identify, e.g., 65%, 70%, 75%, 80%, 85%, 90% or higher.

Also provided are proteins that are substantially identical to the specifically described proteins herein, where by substantially identical is meant that the protein has an amino acid sequence identity to the reference protein of at least about 60%, usually at least about 65% and more usually at least about 70%, where in some instances the identity may be much higher, e.g., 75%, 80%, 85%, 90%, 95% or higher.

In many embodiments, the subject homologues have structural features found in the above provided specific sequences, where such structural features include the β-can fold.

Proteins that are mutants of the specifically described proteins herein are also provided. Mutants may retain biological properties of the wild-type (e.g., naturally occurring) proteins, or may have biological properties that differ from the wild-type proteins. The term "biological property" of the subject proteins includes, but is not limited to, spectral properties, such as absorbance maximum, emission maximum, maximum extinction coefficient, brightness (e.g., as compared to the wild-type protein or another reference protein such as green fluorescent protein from *A. victoria*), and the like; in vivo and/or in vitro stability (e.g., half-life); etc. Mutants include single amino acid changes, deletions of one or more amino acids, N-terminal truncations, C-terminal truncations, insertions, etc.

Mutants can be generated using standard techniques of molecular biology, e.g., random mutagenesis, and targeted mutagenesis. Several mutants are described herein. Given the guidance provided in the Examples, and using standard techniques, those skilled in the art can readily generate a wide variety of additional mutants and test whether a biological property has been altered. For example, fluorescence intensity can be measured using a spectrophotometer at various excitation wavelengths.

Those proteins of the subject invention that are naturally occurring proteins are present in a non-naturally occurring environment, e.g., are separated from their naturally occurring environment. In certain embodiments, the subject proteins are present in a composition that is enriched for the subject protein as compared to its naturally occurring environment. For example, purified protein is provided, where by purified is meant that the protein is present in a composition that is substantially free of non-chromo/fluoroprotein proteins of interest, where by substantially free is meant that less than 90%, usually less than 60% and more usually less than 50% of the composition is made up of non-chromoproteins or mutants thereof of interest. The proteins of the subject invention may also be present as an isolate, by which is meant that the protein is substantially free of other proteins and other naturally occurring biologic molecules, such as oligosaccharides, polynucleotides and fragments thereof, and the like, where the term "substantially free" in this instance means that less than 70%, usually less than 60% and more usually less than 50% of the composition containing the isolated protein is some other-naturally occurring biological molecule. In certain embodiments, the proteins are present in substantially pure form, where by "substantially pure form" is meant at least 95%, usually at least 97% and more usually at least 99% pure.

In addition to the specifically described proteins herein, polypeptides that vary from these proteins, e.g., the mutant proteins described above, are also provided. Generally such polypeptides include an amino acid sequence encoded by an open reading frame (ORF) of the gene encoding the subject wild type protein, including the full length protein and fragments thereof, particularly biologically active fragments and/ or fragments corresponding to functional domains, and the like; and including fusions of the subject polypeptides to other proteins or parts thereof. Fragments of interest will typically be at least about 10 aa in length, usually at least about 50 aa in length, and may be as long as 300 aa in length or longer, but will usually not exceed about 1000 aa in length, where the fragment will have a stretch of amino acids that is identical to the subject protein of at least about 10 aa, and usually at least about 15 aa, and in many embodiments at least about 50 aa in length. In some embodiments, the subject polypeptides are about 25 aa, about 50 aa, about 75 aa, about 100 aa, about 125 aa, about 150 aa, about 200 aa, about 210 aa, about 220 aa, about 230 aa, or about 240 aa in length, up to the entire protein. In some embodiments, a protein fragment retains all or substantially all of a biological property of the wild-type protein.

The subject proteins and polypeptides may be obtained from naturally occurring sources or synthetically produced. For example, wild type proteins may be derived from biological sources which express the proteins, e.g., non-bioluminescent *Cnidarian*, e.g., *Anthozoan*, species, such as the specific ones listed above. The subject proteins may also be derived from synthetic means, e.g., by expressing a recombinant gene or nucleic acid coding sequence encoding the protein of interest in a suitable host, as described above. Any convenient protein purification procedures may be employed, where suitable protein purification methodologies are described in Guide to Protein Purification, (Deuthser ed.) (Academic Press, 1990). For example, a lysate may prepared from the original source and purified using HPLC, exclusion chromatography, gel electrophoresis, affinity chromatography, and the like.

Antibody Compositions

Also provided are antibodies that specifically bind to the subject fluorescent proteins. Suitable antibodies are obtained by immunizing a host animal with peptides comprising all or a portion of the subject protein. Suitable host animals include mouse, rat sheep, goat, hamster, rabbit, etc. The origin of the protein immunogen will generally be a *Cnidarian* species, specifically a non-bioluminescent *Cnidarian* species, such as an *Anthozoan* species or a non-*Petalucean Anthozoan* species. The host animal will generally be a different species than the immunogen, e.g., mice, etc.

The immunogen may comprise the complete protein, or fragments and derivatives thereof. Preferred immunogens comprise all or a part of the protein, where these residues contain the post-translation modifications found on the native target protein. Immunogens are produced in a variety of ways known in the art, e.g., expression of cloned genes using conventional recombinant methods, isolation from *Anthozoan* species of origin, etc.

For preparation of polyclonal antibodies, the first step is immunization of the host animal with the target protein, where the target protein will preferably be in substantially pure form, comprising less than about 1% contaminant. The immunogen may comprise the complete target protein, fragments or derivatives thereof. To increase the immune response of the host animal, the target protein may be combined with an adjuvant, where suitable adjuvants include alum, dextran, sulfate, large polymeric anions, oil & water emulsions, e.g. Freund's adjuvant, Freund's complete adjuvant, and the like. The target protein may also be conjugated to synthetic carrier proteins or synthetic antigens. A variety of hosts may be immunized to produce the polyclonal antibodies. Such hosts include rabbits, guinea pigs, rodents, e.g. mice, rats, sheep, goats, and the like. The target protein is administered to the host, usually intradermally, with an initial dosage followed by one or more, usually at least two, additional booster dosages. Following immunization, the blood from the host will be collected, followed by separation of the serum from the blood cells. The Ig present in the resultant antiserum may be further fractionated using known methods, such as ammonium salt fractionation, DEAE chromatography, and the like.

Monoclonal antibodies are produced by conventional techniques. Generally, the spleen and/or lymph nodes of an immunized host animal provide a source of plasma cells. The plasma cells are immortalized by fusion with myeloma cells to produce hybridoma cells. Culture supernatant from individual hybridomas is screened using standard techniques to identify those producing antibodies with the desired specificity. Suitable animals for production of monoclonal antibodies to the human protein include mouse, rat, hamster, etc. To raise antibodies against the mouse protein, the animal will generally be a hamster, guinea pig, rabbit, etc. The antibody may be purified from the hybridoma cell supernatants or ascites fluid by conventional techniques, e.g. affinity chromatography using protein bound to an insoluble support, protein A sepharose, etc.

The antibody may be produced as a single chain, instead of the normal multimeric structure. Single chain antibodies are described in Jost et al. (1994) *J.B.C.* 269:26267-73, and others. DNA sequences encoding the variable region of the heavy chain and the variable region of the light chain are ligated to a spacer encoding at least about 4 amino acids of small neutral amino acids, including glycine and/or serine. The protein encoded by this fusion allows assembly of a functional variable region that retains the specificity and affinity of the original antibody.

Also of interest in certain embodiments are humanized antibodies. Methods of humanizing antibodies are known in the art. The humanized antibody may be the product of an animal having transgenic human immunoglobulin constant region genes (see for example International Patent Applications WO 90/10077 and WO 90/04036). Alternatively, the antibody of interest may be engineered by recombinant DNA techniques to substitute the CH1, CH2, CH3, hinge domains, and/or the framework domain with the corresponding human sequence (see WO 92/02190).

The use of Ig cDNA for construction of chimeric immunoglobulin genes is known in the art (Liu et al. (1987) *P.N.A.S.* 84:3439 and (1987) *J. Immunol.* 139:3521). mRNA is isolated from a hybridoma or other cell producing the antibody and used to produce cDNA. The cDNA of interest may be amplified by the polymerase chain reaction using specific primers (U.S. Pat. Nos. 4,683,195 and 4,683,202). Alternatively, a library is made and screened to isolate the sequence of interest. The DNA sequence encoding the variable region of the antibody is then fused to human constant region sequences. The sequences of human constant regions genes may be found in Kabat et al. (1991) *Sequences of Proteins of Immunological Interest*, N.I.H. publication no. 91-3242. Human C region genes are readily available from known clones. The choice of isotype will be guided by the desired effector functions, such as complement fixation, or activity in antibody-dependent cellular cytotoxicity. Preferred isotypes are IgG1, IgG3 and IgG4. Either of the human light chain constant regions, kappa or lambda, may be used. The chimeric, humanized antibody is then expressed by conventional methods.

Antibody fragments, such as Fv, F(ab')$_2$ and Fab may be prepared by cleavage of the intact protein, e.g. by protease or chemical cleavage. Alternatively, a truncated gene is designed. For example, a chimeric gene encoding a portion of the F(ab')$_2$ fragment would include DNA sequences encoding the CH1 domain and hinge region of the H chain, followed by a translational stop codon to yield the truncated molecule.

Consensus sequences of H and L J regions may be used to design oligonucleotides for use as primers to introduce useful restriction sites into the J region for subsequent linkage of V region segments to human C region segments. C region cDNA can be modified by site directed mutagenesis to place a restriction site at the analogous position in the human sequence.

Expression vectors include plasmids, retroviruses, YACs, EBV derived episomes, and the like. A convenient vector is one that encodes a functionally complete human CH or CL immunoglobulin sequence, with appropriate restriction sites engineered so that any VH or VL sequence can be easily inserted and expressed. In such vectors, splicing usually occurs between the splice donor site in the inserted J region and the splice acceptor site preceding the human C region, and also at the splice regions that occur within the human CH exons. Polyadenylation and transcription termination occur at native chromosomal sites downstream of the coding regions. The resulting chimeric antibody may be joined to any strong promoter, including retroviral LTRs, e.g. SV-40 early promoter, (Okayama et al. (1983) *Mol. Cell. Bio.* 3:280), Rous sarcoma virus LTR (Gorman et al. (1982) *P.N.A.S.* 79:6777), and moloney murine leukemia virus LTR (Grosschedl et al. (1985) *Cell* 41:885); native Ig promoters, etc.

Transgenics

The subject nucleic acids can be used to generate transgenic, non-human plants or animals or site specific gene modifications in cell lines. Transgenic cells of the subject invention include on or more nucleic acids according to the subject invention present as a transgene, where included within this definition are the parent cells transformed to include the transgene and the progeny thereof. In many embodiments, the transgenic cells are cells that do not normally harbor or contain a nucleic acid according to the subject invention. In those embodiments where the transgenic cells do naturally contain the subject nucleic acids, the nucleic acid will be present in the cell in a position other than its natural location, i.e. integrated into the genomic material of the cell at a non-natural location. Transgenic animals may be made through homologous recombination, where the endogenous locus is altered. Alternatively, a nucleic acid construct is randomly integrated into the genome. Vectors for stable integration include plasmids, retroviruses and other animal viruses, YACs, and the like.

Transgenic organisms of the subject invention include cells and multicellular organisms, e.g., plants and animals, that are endogenous knockouts in which expression of the endogenous gene is at least reduced if not eliminated. Transgenic organisms of interest also include cells and multicellular organisms, e.g., plants and animals, in which the protein or variants thereof is expressed in cells or tissues where it is not normally expressed and/or at levels not normally present in such cells or tissues.

DNA constructs for homologous recombination will comprise at least a portion of the gene of the subject invention, wherein the gene has the desired genetic modification(s), and includes regions of homology to the target locus. DNA constructs for random integration need not include regions of homology to mediate recombination. Conveniently, markers for positive and negative selection are included. Methods for generating cells having targeted gene modifications through homologous recombination are known in the art. For various techniques for transfecting mammalian cells, see Keown et al. (1990), *Meth. Enzymol.* 185:527-537.

For embryonic stem (ES) cells, an ES cell line may be employed, or embryonic cells may be obtained freshly from a host, e.g. mouse, rat, guinea pig, etc. Such cells are grown on an appropriate fibroblast-feeder layer or grown in the presence of leukemia inhibiting factor (LIF). When ES or embryonic cells have been transformed, they may be used to produce transgenic animals. After transformation, the cells are plated onto a feeder layer in an appropriate medium. Cells containing the construct may be detected by employing a selective medium. After sufficient time for colonies to grow, they are picked and analyzed for the occurrence of homologous recombination or integration of the construct. Those colonies that are positive may then be used for embryo manipulation and blastocyst injection. Blastocysts are obtained from 4 to 6 week old superovulated females. The ES cells are trypsinized, and the modified cells are injected into the blastocell of the blastocyst. After injection, the blastocysts are returned to each uterine horn of pseudopregnant females. Females are then allowed to go to term and the resulting offspring screened for the construct. By providing for a different phenotype of the blastocyst and the genetically modified cells, chimeric progeny can be readily detected.

The chimeric animals are screened for the presence of the modified gene and males and females having the modification are mated to produce homozygous progeny. If the gene alterations cause lethality at some point in development, tissues or organs can be maintained as allogeneic or congenic grafts or transplants, or in in vitro culture. The transgenic animals may be any non-human mammal, such as laboratory animals, domestic animals, etc. The transgenic animals may be used in functional studies, drug screening, etc. Representative examples of the use of transgenic animals include those described infra.

Transgenic plants may be produced in a similar manner. Methods of preparing transgenic plant cells and plants are described in U.S. Pat. Nos. 5,767,367; 5,750,870; 5,739,409; 5,689,049; 5,689,045; 5,674,731; 5,656,466; 5,633,155; 5,629,470; 5,595,896; 5,576,198; 5,538,879; 5,484,956; the disclosures of which are herein incorporated by reference. Methods of producing transgenic plants are also reviewed in Plant Biochemistry and Molecular Biology (eds Lea & Leegood, John Wiley & Sons)(1993) pp 275-295. In brief, a suitable plant cell or tissue is harvested, depending on the nature of the plant species. As such, in certain instances, protoplasts will be isolated, where such protoplasts may be isolated from a variety of different plant tissues, e.g. leaf, hypoctyl, root, etc. For protoplast isolation, the harvested cells are incubated in the presence of cellulases in order to remove the cell wall, where the exact incubation conditions vary depending on the type of plant and/or tissue from which the cell is derived. The resultant protoplasts are then separated from the resultant cellular debris by sieving and centrifugation. Instead of using protoplasts, embryogenic explants comprising somatic cells may be used for preparation of the transgenic host. Following cell or tissue harvesting, exogenous DNA of interest is introduced into the plant cells, where a variety of different techniques are available for such introduction. With isolated protoplasts, the opportunity arise for introduction via DNA-mediated gene transfer protocols, including: incubation of the protoplasts with naked DNA, e.g. plasmids, comprising the exogenous coding sequence of interest in the presence of polyvalent cations, e.g. PEG or PLO; and electroporation of the protoplasts in the presence of naked DNA comprising the exogenous sequence of interest. Protoplasts that have successfully taken up the exogenous DNA are then selected, grown into a callus, and ultimately into a transgenic plant through contact with the appropriate amounts and ratios of stimulatory factors, e.g. auxins and cytokinins. With embryogenic explants, a convenient method of introducing the exogenous DNA in the target somatic cells is through the use of particle acceleration or "gene-gun" protocols. The resultant explants are then allowed to grow into chimera plants, cross-bred and transgenic progeny are obtained. Instead of the naked DNA approaches described above, another convenient method of producing transgenic plants is *Agrobacterium* mediated transformation. With *Agrobacterium* mediated transformation, co-integrative or binary vectors comprising the exogenous DNA are prepared and then introduced into an appropriate *Agrobacterium* strain, e.g. *A. tumefaciens*. The resultant bacteria are then incubated with prepared protoplasts or tissue explants, e.g. leaf disks, and a callus is produced. The callus is then grown under selective conditions, selected and subjected to growth media to induce root and shoot growth to ultimately produce a transgenic plant.

Utility

The subject chromoproteins and fluorescent mutants thereof find use in a variety of different applications, where the applications necessarily differ depending on whether the protein is a chromoprotein or a fluorescent protein. Representative uses for each of these types of proteins will be described below, where the follow described uses are merely representative and are in no way meant to limit the use of the subject proteins to those described below.

Chromoproteins

The subject chromoproteins of the present invention find use in a variety of different applications. One application of interest is the use of the subject proteins as coloring agents which are capable of imparting color or pigment to a particular composition of matter. Of particular interest in certain embodiments are non-toxic chromoproteins. The subject chromoproteins may be incorporated into a variety of different compositions of matter, where representative compositions of matter include: food compositions, pharmaceuticals, cosmetics, living organisms, e.g., animals and plants, and the like. Where used as a coloring agent or pigment, a sufficient amount of the chromoprotein is incorporated into the composition of matter to impart the desired color or pigment thereto. The chromoprotein may be incorporated into the composition of matter using any convenient protocol, where the particular protocol employed will necessarily depend, at least in part, on the nature of the composition of matter to be colored. Protocols that may be employed include, but are not limited to: blending, diffusion, friction, spraying, injection, tattooing, and the like.

The chromoproteins may also find use as labels in analyte detection assays, e.g., assays for biological analytes of interest. For example, the chromoproteins may be incorporated into adducts with analyte specific antibodies or binding fragments thereof and subsequently employed in immunoassays for analytes of interest in a complex sample, as described in U.S. Pat. No. 4,302,536; the disclosure of which is herein incorporated by reference. Instead of antibodies or binding fragments thereof, the subject chromoproteins or chromogenic fragments thereof may be conjugated to ligands that specifically bind to an analyte of interest, or other moieties, growth factors, hormones, and the like; as is readily apparent to those of skill in the art.

In yet other embodiments, the subject chromoproteins may be used as selectable markers in recombinant DNA applications, e.g., the production of transgenic cells and organisms, as described above. As such, one can engineer a particular transgenic production protocol to employ expression of the subject chromoproteins as a selectable marker, either for a successful or unsuccessful protocol. Thus, appearance of the color of the subject chromoprotein in the phenotype of the transgenic organism produced by a particular process can be used to indicate that the particular organism successfully harbors the transgene of interest, often integrated in a manner that provides for expression of the transgene in the organism. When used a selectable marker, a nucleic acid encoding for the subject chromoprotein can be employed in the transgenic generation process, where this process is described in greater detail supra. Particular transgenic organisms of interest where the subject proteins may be employed as selectable markers include transgenic plants, animals, bacteria, fungi, and the like.

In yet other embodiments, the chromoproteins (and fluorescent proteins) of the subject invention find use in sunscreens, as selective filters, etc., in a manner similar to the uses of the proteins described in WO 00/46233.

Fluorescent Proteins

The subject fluorescent proteins of the present invention (as well as other components of the subject invention described above) find use in a variety of different applications, where such applications include, but are not limited to, the following. The first application of interest is the use of the subject proteins in fluorescence resonance energy transfer (FRET) applications. In these applications, the subject proteins serve as donor and/or acceptors in combination with a second fluorescent protein or dye, e.g., a fluorescent protein as described in Matz et al., Nature Biotechnology (October 1999) 17:969-973, a green fluorescent protein from *Aequoria victoria* or fluorescent mutant thereof, e.g., as described in U.S. Pat. Nos. 6,066,476; 6,020,192; 5,985,577; 5,976,796; 5,968,750; 5,968,738; 5,958,713; 5,919,445; 5,874,304, the disclosures of which are herein incorporated by reference, other fluorescent dyes, e.g., coumarin and its derivatives, e.g. 7-amino-4-methylcoumarin, aminocoumarin, bodipy dyes, such as Bodipy FL, cascade blue, fluorescein and its derivatives, e.g. fluorescein isothiocyanate, Oregon green, rhodamine dyes, e.g. texas red, tetramethylrhodamine, eosins and erythrosins, cyanine dyes, e.g. Cy3 and Cy5, macrocyclic chelates of lanthanide ions, e.g. quantum dye, etc., chemilumescent dyes, e.g., luciferases, including those described in U.S. Pat. Nos. 5,843,746; 5,700,673; 5,674,713; 5,618,722; 5,418,155; 5,330,906; 5,229,285; 5,221,623; 5,182,202; the disclosures of which are herein incorporated by reference. Specific examples of where FRET assays employing the subject fluorescent proteins may be used include, but are not limited to: the detection of protein-protein interactions, e.g., mammalian two-hybrid system, transcription factor dimerization, membrane protein multimerization, multiprotein complex formation, etc., as a biosensor for a number of different events, where a peptide or protein covalently links a FRET fluorescent combination including the subject fluorescent proteins and the linking peptide or protein is, e.g., a protease specific substrate, e.g., for caspase mediated cleavage, a linker that undergoes conformational change upon receiving a signal which increases or decreases FRET, e.g., PKA regulatory domain (cAMP-sensor), phosphorylation, e.g., where there is a phosphorylation site in the linker or the linker has binding specificity to phosphorylated/dephosphorylated domain of another protein, or the linker has $Ca^{2+}$ binding domain. Representative fluorescence resonance energy transfer or FRET applications in which the subject proteins find use include, but are not limited to, those described in: U.S. Pat. Nos. 6,008,373; 5,998,146; 5,981,200; 5,945,526; 5,945,283; 5,911,952; 5,869,255; 5,866,336; 5,863,727; 5,728,528; 5,707,804; 5,688,648; 5,439,797; the disclosures of which are herein incorporated by reference.

The subject fluorescent proteins also find use as biosensors in prokaryotic and eukaryotic cells, e.g. as $Ca^{2+}$ ion indicator; as pH indicator, as phorphorylation indicator, as an indicator of other ions, e.g., magnesium, sodium, potassium, chloride and halides. For example, for detection of Ca ion, proteins containing an EF-hand motif are known to translocate from the cytosol to membranes upon $Ca^{2+}$ binding. These proteins contain a myristoyl group that is buried within the molecule by hydrophobic interactions with other regions of the protein. Binding of $Ca^{2+}$ induces a conformational change exposing the myristoyl group which then is available for the insertion into the lipid bilayer (called a "$Ca^{2+}$-myristoyl switch"). Fusion of such a EF-hand containing protein to Fluorescent Proteins (FP) could make it an indicator of intracellular $Ca^{2+}$ by monitoring the translocation from the cytosol to the plasma membrane by confocal microscopy. EF-hand proteins suitable for use in this system include, but are not limited to: recoverin (1-3), calcineurin B, troponin C, visinin, neurocalcin, calmodulin, parvalbumin, and the like. For pH, a system based on hisactophilins may be employed. Hisactophilins are myristoylated histidine-rich proteins known to exist in *Dictyostelium*. Their binding to actin and acidic lipids is sharply pH-dependent within the range of cytoplasmic pH variations. In living cells membrane binding seems to override the interaction of hisactophilins with actin filaments. At pH≤6.5 they locate to the plasma membrane and nucleus. In contrast, at pH 7.5 they evenly distribute throughout the cytoplasmic space. This change of distribution is reversible and is attributed to histidine clusters exposed in loops on the surface of the molecule. The reversion of intracellular distribution in the range of cytoplasmic pH variations is in accord with a pK of 6.5 of histidine residues. The cellular distribution is independent of myristoylation of the protein. By fusing FPs (Fluoresent Proteins) to hisactophilin the intracellular distribution of the fusion protein can be followed by laser scanning, confocal microscopy or standard fluorescence microscopy. Quantitative fluorescence analysis can be done by performing line scans through cells (laser scanning confocal microscopy) or other electronic data analysis (e.g., using metamorph software (Universal Imaging Corp) and averaging of data collected in a population of cells. Substantial pH-dependent redistribution of hisactophilin-FP from the cytosol to the plasma membrane occurs within 1-2 min and reaches a steady state level after 5-10 min. The reverse reaction takes place on a similar time scale. As such, hisactophilin-fluorescent protein fusion protein that acts in an analogous fashion can be used to monitor cytosolic pH changes in real time in live mammalian cells. Such methods have use in high throuhgput applications, e.g., in the measurement of pH changes as consequence of growth factor receptor activation (e.g. epithelial or platelet-derived growth factor) chemotactic stimulation/ cell locomotion, in the detection of intracellular pH changes as second messenger, in the monitoring of intracellular pH in pH manipulating experiments, and the like. For detection of PKC activity, the reporter system exploits the fact that a molecule called MARCKS (myristoylated alanine-rich C kinase substrate) is a PKC substrate. It is anchored to the plasma membrane via myristoylation and a stretch of positively charged amino acids (ED-domain) that bind to the negatively charged plasma membrane via electrostatic interactions. Upon PKC activation the ED-domain becomes phosphorylated by PKC, thereby becoming negatively charged, and as a consequence of electrostatic repulsion MARCKS translocates from the plasma membrane to the cytoplasm (called the "myristoyl-electrostatic switch"). Fusion of the N-terminus of MARCKS ranging from the myristoylation motif to the ED-domain of MARCKS to fluorescent proteins of the present invention makes the above a detector system for PKC activity. When phosphorylated by PKC, the fusion protein translocates from the plasma membrane to the cytosol. This translocation is followed by standard fluorescence microscopy or confocal microscopy e.g. using the Cellomics technology or other High Content Screening systems (e.g. Universal Imaging Corp./Becton Dickinson). The above reporter system has application in High Content Screening, e.g., screening for PKC inhibitors, and as an indicator for PKC activity in many screening scenarios for potential reagents interfering with this signal transduction pathway. Methods of using fluorescent proteins as biosensors also include those described in U.S. Pat. Nos. 972,638; 5,824,485 and 5,650,135 (as well as the references cited therein) the disclosures of which are herein incorporated by reference.

The subject fluorescent proteins also find use in applications involving the automated screening of arrays of cells expressing fluorescent reporting groups by using microscopic imaging and electronic analysis. Screening can be used for drug discovery and in the field of functional genomics: e.g., where the subject proteins are used as markers of whole cells to detect changes in multicellular reorganization and migration, e.g., formation of multicellular tubules (blood vessel formation) by endothelial cells, migration of cells through Fluoroblok Insert System (Becton Dickinson Co.), wound healing, neurite outgrowth, etc.; where the proteins are used as markers fused to peptides (e.g., targeting sequences) and proteins that allow the detection of change of intracellular location as indicator for cellular activity, for example: signal transduction, such as kinase and transcription factor translocation upon stimuli, such as protein kinase C, protein kinase A, transcription factor NFkB, and NFAT; cell cycle proteins, such as cyclin A, cyclin B1 and cyclin E; protease cleavage with subsequent movement of cleaved substrate, phospholipids, with markers for intracellular structures such as endoplasmic reticulum, *Golgi* apparatus, mitochondria, peroxisomes, nucleus, nucleoli, plasma membrane, histones, endosomes, lysosomes, microtubules, actin) as tools for High Content Screening: co-localization of other fluorescent fusion proteins with these localization markers as indicators of movements of intracellular fluorescent fusion proteins/peptides or as marker alone; and the like. Examples of applications involving the automated screening of arrays of cells in which the subject fluorescent proteins find use include: U.S. Pat. No. 5,989,835; as well as WO/0017624; WO 00/26408; WO 00/17643; and WO 00/03246; the disclosures of which are herein incorporated by reference.

The subject fluorescent proteins also find use in high through-put screening assays. The subject fluorescent proteins are stable proteins with half-lives of more than 24 h. Also provided are destabilized versions of the subject fluorescent proteins with shorter half-lives that can be used as transcription reporters for drug discovery. For example, a protein according to the subject invention can be fused with a putative proteolytic signal sequence derived from a protein with shorter half-life, e.g., PEST sequence from the mouse ornithine decarboxylase gene, mouse cyclin B1 destruction box and ubiquitin, etc. For a description of destabilized proteins and vectors that can be employed to produce the same, see e.g., U.S. Pat. No. 6,130,313; the disclosure of which is herein incorporated by reference. Promoters in signal transduction pathways can be detected using destabilized versions of the subject fluorescent proteins for drug screening, e.g., AP1, NFAT, NFkB, Smad, STAT, p53, E2F, Rb, myc, CRE, ER, GR and TRE, and the like.

The subject proteins can be used as second messenger detectors, e.g., by fusing the subject proteins to specific domains: e.g., PKCgamma Ca binding domain, PKCgamma DAG binding domain, SH2 domain and SH3 domain, etc.

Secreted forms of the subject proteins can be prepared, e.g. by fusing secreted leading sequences to the subject proteins to construct secreted forms of the subject proteins, which in turn can be used in a variety of different applications.

The subject proteins also find use in fluorescence activated cell sorting applications. In such applications, the subject fluorescent protein is used as a label to mark a population of cells and the resulting labeled population of cells is then sorted with a fluorescent activated cell sorting device, as is known in the art. FACS methods are described in U.S. Pat. Nos. 5,968,738 and 5,804,387; the disclosures of which are herein incorporated by reference.

The subject proteins also find use as in vivo marker in animals (e.g., transgenic animals). For example, expression of the subject protein can be driven by tissue specific promoters, where such methods find use in research for gene therapy, e.g., testing efficiency of transgenic expression, among other applications. A representative application of fluorescent proteins in transgenic animals that illustrates this class of applications of the subject proteins is found in WO 00/02997, the disclosure of which is herein incorporated by reference.

Additional applications of the subject proteins include: as markers following injection into cells or animals and in calibration for quantitative measurements (fluorescence and protein); as markers or reporters in oxygen biosensor devices for monitoring cell viability; as markers or labels for animals, pets, toys, food, etc.; and the like.

The subject fluorescent proteins also find use in protease cleavage assays. For example, cleavage inactivated fluorescence assays can be developed using the subject proteins, where the subject proteins are engineered to include a protease specific cleavage sequence without destroying the fluorescent character of the protein. Upon cleavage of the fluorescent protein by an activated protease fluorescence would sharply decrease due to the destruction of a functional chromophor. Alternatively, cleavage activated fluorescence can be developed using the subject proteins, where the subject proteins are engineered to contain an additional spacer sequence in close proximity/or inside the chromophor. This variant would be significantly decreased in its fluorescent activity, because parts of the functional chromophor would be divided by the spacer. The spacer would be framed by two identical protease specific cleavage sites. Upon cleavage via the activated protease the spacer would be cut out and the two residual "subunits" of the fluorescent protein would be able to reassemble to generate a functional fluorescent protein. Both of the above types of application could be developed in assays for a variety of different types of proteases, e.g., caspases, etc.

The subject proteins can also be used is assays to determine the phospholipid composition in biological membranes. For example, fusion proteins of the subject proteins (or any other kind of covalent or non-covalent modification of the subject proteins) that allows binding to specific phospholipids to localize/visualize patterns of phospholipid distribution in biological membranes also allowing colocalization of membrane proteins in specific phospholipid rafts can be accomplished with the subject proteins. For example, the PH domain of GRP1 has a high affinity to phosphatidyl-inositol tri-phosphate (PIP3) but not to PIP2. As such, a fusion protein between the PH domain of GRP1 and the subject proteins can be constructed to specifically label PIP3 rich areas in biological membranes.

Yet another application of the subject proteins is as a fluorescent timer, in which the switch of one fluorescent color to another (e.g. green to red) concomitant with the ageing of the fluorescent protein is used to determine the activation/deactivation of gene expression, e.g., developmental gene expression, cell cycle dependent gene expression, circadian rhythm specific gene expression, and the like The antibodies of the subject invention, described above, also find use in a number of applications, including the differentiation of the subject proteins from other fluorescent proteins.

Kits

Also provided by the subject invention are kits for use in practicing one or more of the above described applications, where the subject kits typically include elements for making the subject proteins, e.g., a construct comprising a vector that includes a coding region for the subject protein. The subject kit components are typically present in a suitable storage medium, e.g., buffered solution, typically in a suitable container. Also present in the subject kits may be antibodies to the provided protein. In certain embodiments, the kit comprises a plurality of different vectors each encoding the subject protein, where the vectors are designed for expression in different environments and/or under different conditions, e.g., constitutive expression where the vector includes a strong promoter for expression in mammalian cells, a promoterless vector with a multiple cloning site for custom insertion of a promoter and tailored expression, etc.

In addition to the above components, the subject kits will further include instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e.g., diskette, CD, etc., on which the information has been recorded. Yet another means that may be present is a website address which may be used via the internet to access the information at a removed site. Any convenient means may be present in the kits.

The following examples are offered by way of illustration and not by way of limitation.

EXPERIMENTAL

I. Introduction

The red fluorescent protein DsRed has spectral properties that are ideal for dual-color experiments with green fluorescent protein (GFP). But wild-type DsRed has several drawbacks, including slow chromophore maturation and poor solubility. To overcome the slow maturation, we used random and directed mutagenesis to create DsRed variants that mature 10-15 times faster than the wild-type protein. An asparagine-to-glutamine substitution at position 42 greatly accelerates the maturation of DsRed, but also increases the level of green emission. Additional amino acid substitutions suppress this green emission while further accelerating the maturation. To enhance the solubility of DsRed, the net charge near the N terminus of the protein was reduced. The resultant DsRed variants yield bright fluorescence even in rapidly growing organisms such as yeast.

II. Experimental Protocol

A. Mutagenesis and Screening

For mutagenesis, a wild-type or mutant DsRed gene present in the pDsRed1-N1 vector (Clontech, Palo Alto, Calif.) was excised with NheI and HpaI and used as a template for error-prone PCR (Cadwell, R. C. & Joyce, G. F. In *PCR Primer. A laboratory manual*. (eds Dieffenbach, C. W. & Dveksler, G. S.) 583-589 (Cold Spring Harbor Laboratory Press, Cold Spring Harbor, N.Y.; 1995)). The amplified product was digested with BamHI and BsaBI, gel purified, and ligated between the BamHI and EcI136II sites of the pQE31 expression vector (Qiagen, Valencia, Calif.), which encodes an N-terminal hexahistidine tag. The library of mutated DsRed genes was transformed into *E. coli* strain DH10B. For rounds 1-3 of the mutagenesis, 50,000-100,000 colonies were screened for bright fluorescence using the slide projector assay described in the text. For round 4, 4,000 brightly fluorescent colonies were picked into wells of 96-well plates, then grown to saturation, lysed with B-PER II reagent (Pierce, Rockford, Ill.), and centrifuged for 5 min at 2,500 g. The supernatants were transferred to a second set of 96-well plates, and the fluorescence signals from the pellets and supernatants were compared visually using the slide projector assay. Clones that showed an elevated ratio of soluble to insoluble fluorescence were analyzed further. For round 5, 10 pools of 10,000 mutant clones each were recovered from the transformation plates and subjected to cell sorting using a Becton Dickinson FACStarPlus flow cytometer. Fluorescence signals were measured simultaneously in the green (FL-1) and red (FL-2) channels, and cells were collected if they showed strong red fluorescence but reduced green fluorescence.

B. Purification and Spectral Analysis of the DsRed Variants.

To purify the hexa-histidine-tagged proteins, a fluorescent protein gene in the pQE31 vector was transformed into *E. coli* cells carrying the pREP4 repressor plasmid (Qiagen). A 250 ml culture was grown to an OD600 of 0.5 and then induced with 1 mM isopropyl-β-D-thiogalactoside (IPTG) for 6-8 h at 37° C. The cells were lysed with 10 ml of B-PER II and centrifuged for 20 min at 27,000 g. Detergent was removed from the supernatant by adding NaCl to 300 mM and centrifuging for 10 min at 2,500 g. After adding 1 ml of $Ni^{2+}$-NTA-agarose beads (Qiagen), the tube was mixed end-over-end for 1 h. The beads were washed three times with 10 ml of 300 mM NaCl, 20 mM imidazole-HCl, pH 7.4, 0.5% Triton X-100, and then three times with the same buffer lacking Triton X-100. The fluorescent protein was eluted with 2.5 ml of 300 mM imidazole-HCl, pH 7.4, and dialyzed into 50 mM $Na^+$-HEPES, pH 7.5, 100 mM NaCl, 1 mM EDTA.

Corrected excitation and emission spectra of purified DsRed variants, diluted to an A558 of <0.04 in $Na^+$-HEPES, pH 7.5, 100 mM NaCl, 1 mM EDTA, were acquired with a Horiba FluoroMax-3 spectrofluorometer. The scanning windows were 1 nM. Emission was measured at 600 nm for the excitation spectra, and excitation was at 470 nm for the emission spectra. To determine extinction coefficients, the fluorescent protein concentrations were assayed using the BCA method (Pierce), and the absorbances of the proteins at their excitation maxima were measured using a Spectronic Unicam GENESYS 10 UV spectrophotometer. Quantum yields were determined as described (Baird, et al., *Proc. Natl. Acad. Sci. USA* 97, 11984-11989 (2000); Lakowicz, J. R. *Principles of fluorescence spectroscopy*, Edn. 2. (Kluwer Academic/Plenum Publishers, New York, N.Y.; 1999)) using ethanolic rhodamine 101 as a reference; for these measurements the excitation wavelength was 535 nm and the fluorescence emission as integrated from 550-800 nm.

C. Measurement of Maturation Kinetics.

Genes encoding the DsRed variants were cloned into the pQE81 expression vector (Qiagen) and transformed into *E. coli*. Bacterial cultures growing with aeration at 37° C. were induced with 1 mM IPTG for 30 min to generate a pulse of expression for each DsRed variant. A chase was then initiated by inhibiting protein synthesis with a mixture of 170 μg/ml chloramphenicol, 30 μg/ml kanamycin, and 50 μg/ml tetracycline. At the designated time points, aliquots of the cultures were removed, adjusted to 15% glycerol, and frozen at −80° C. These aliquots were later thawed rapidly and evaluated using a Becton Dickinson FACScan flow cytometer to determine the average intensity of red fluorescence (channel FL-2) per cell. A portion of each aliquot was precipitated with trichloroacetic acid, then subjected to SDS-PAGE and immunoblotting with an anti-hexahistidine monoclonal antibody (Qiagen) to measure the total amount of DsRed polypeptide in the cultures. Fluorescence microscopy of yeast. A CEN plasmid derived from pRS315 (Sikorski, *Genetics* 122, 19-27 (1989)) and carrying a pCox4-DsRed1 fusion gene under the control of the ADH1 promoter was used. Derivatives of this plasmid were created by replacing the DsRed1 coding sequence with the coding sequence of DsRed.T3 or DsRed.T4. These plasmids were introduced into *S. cerevisiae* strain BGY101, which carries a chromosomal SEC7-EGFPx3 gene 20. Cells from the resulting yeast strains were grown in minimal glucose medium and fixed, and projected fluorescence images were acquired as described Rossanese et al., *J. Cell Biol.* 145, 69-81 (1999).

III. Results and Discussion

A family of fluorescent proteins has recently been described. The most useful of these newly discovered proteins is DsRed, which is derived from the coral *Discosoma*. DsRed has an orange-red fluorescence with an emission maximum at 583 nm. Biophysical and X-ray crystallographic studies revealed that DsRed forms a stable tetramer, and that each monomer is structurally very similar to GFP. The red-shifted fluorescence of DsRed relative to GFP results from a chromophore with a more extensive conjugated π-system. DsRed fluorescence is excited optimally at 558 nm, but can also be excited by a standard 488 nm laser, allowing DsRed to be used with laser-based confocal micro-scopes and flow cytometers. DsRed has a high quantum yield and is photostable. These characteristics make DsRed an ideal candidate for fluorescence imaging, particularly for multicolor experiments involving GFP and its variants. A codon-optimized version of DsRed is now available under the name DsRed1.

Despite these advantages, wild-type DsRed has several problems for use as a fluorescent reporter. When DsRed is fused to another protein, tetramerization of the DsRed domain can perturb the function and localization of the protein. The DsRed tetramer also self-associates to form higher-order aggregates. Perhaps the most serious problem with DsRed is that chromophore maturation is slow, with a half-time of >24 h at room temperature. Newly synthesized DsRed develops a dim green fluorescence by forming the same chromophore that is present in GFP. A second oxidation reaction then generates the red chromophore. This slow maturation has been put to use with a DsRed variant termed the "fluorescent timer", in which the fluorescence of the initial green species is enhanced. However, for most applications the slow maturation of DsRed is not desirable. In dual-label imaging with GFP, the initial green fluorescence of DsRed produces bleed-through into the GFP channel. More generally, the slow development of red fluorescence limits the intensity of the DsRed signal, particularly with rapidly growing organisms such as yeast. A variant termed DsRed2 matures faster than DsRed1, but DsRed2 still requires many hours to attain full fluorescence. Here random and directed mutagenesis was used to create improved variants of DsRed. These new variants mature rapidly, and they are more soluble than wild-type DsRed.

To identify rapidly maturing DsRed variants, an earlier method for visualizing GFP fluorescence in microbial colonies was modified. Hexahistidine-tagged DsRed is produced at high levels in *Escherichia coli*. The fluorescence of the bacterial colonies is excited by placing a 520±20 nm band-pass filter over the lens of a slide projector, and the emission is detected through goggles covered with a Kodak Wratten filter no. 22, which passes wavelengths >550 nm. This technique is simple and efficient.

A library of mutant expression plasmids was generated using error-prone PCR to amplify the DsRed1 template. This library was transformed into *E. coli*, and over 100,000 transformant colonies were examined. Colonies producing the wild-type DsRed1 protein required two days to develop significant fluorescence, but three mutant colonies showed strong fluorescence after one day of growth. Sequencing revealed that the three mutant plasmids were distinct, but that all of them contained an N42H codon change. We therefore generated a variant that had only the N42H substitution.

The N42H variant was purified in parallel with DsRed1, and the two proteins were analyzed by spectrofluorometry. As previously observed, the spectra of purified DsRed1 changed over a period of days as the protein matured (data not shown). By contrast, the spectra of the purified N42H variant remained stable over time (data not shown), consistent with rapid maturation. Unfortunately, in addition to accelerating maturation, the N42H substitution altered the spectral properties of the mature protein (FIG. 1A). Mature DsRed1 is thought to be an equilibrium mixture of red fluorescent molecules and some green fluorescent molecules that are spectrally similar to GFP. The GFP-like species has a blue excitation peak at apporiximately 480 nm and a green emission peak at approximately 500 nm; but DsRed is a tetramer, so excitation of the green molecules often results in fluorescence resonance energy transfer (FRET) with neighboring red molecules to produce red emission. This FRET effect, together with the relatively low percentage of green molecules in mature DsRed1, yields a very small peak of green emission relative to the red emission (FIG. 1A). In the N42H variant, the peaks of blue excitation and green emission were dramatically enhanced (FIG. 1A), indicating that the equilibrium had shifted so that a larger percentage of the mature molecules contained the green chromophore.

Because the N42H substitution considerably increases the size of the side chain, a more conservative N42Q substitution was also tried. This mutation required two base changes and probably would not have been present in the original mutant collection. The N42Q variant retained the rapid maturation property of the N42H variant, but showed much less blue excitation and green emission (FIG. 1A). The N42Q variant was therefore chosen as the starting point for further study.

Additional mutagenesis (see below) yielded DsRed variants that showed even faster maturation and lower green emission than the original N42Q variant. After six rounds of mutagenesis, three optimized variants were selected and termed DsRed.T1, DsRed.T3, and DsRed.T4 (Table 1). The spectral properties of DsRed.T4 (FIG. 1B) are virtually identical to those of DsRed.T1 (data not shown) and very similar to those of the wild-type DsRed1 (FIG. 1A). Compared with DsRed.T1 and DsRed.T4, DsRed.T3 is somewhat brighter (see below) but has a significantly higher peak of blue excitation and a marginally higher peak of green emission (FIG. 1B).

The optimized DsRed variants were examined both in vivo and in vitro. As judged by colony fluorescence, colony size, and plasmid stability, these variants were less toxic to *E. coli* than DsRed1, and they developed fluorescence more efficiently at growth temperatures of 37° C. and higher (data not shown). Like wild-type DsRed, the optimized variants appeared to be tetrameric: they exhibited FRET between the green and red molecules (FIG. 1B), and upon nondenaturing SDS-PAGE they migrated at the position expected for tetramers (see below). With purified DsRed1, we measured an extinction coefficient of 52,000 M−1 cm−1 and a quantum yield of approximately 0.7 (Table 1).

TABLE 1

Properties of the mature DsRed variants[a]

| DsRed variant | Excitation maximum (nm) | Emission maximum (nm) | Maximal extinction coefficient ($M^{-1} cm^{-1}$) | Quantum yield | Relative brightness[b] | Maturation half-time (h)[c] |
|---|---|---|---|---|---|---|
| DsRed1 | 558 | 583 | 52,000 | 0.68 | (1.00) | 11 |
| DsRed2 | 561 | 587 | 43,800 | 0.55 | 0.68 | 6.5 |
| DsRed.T1 | 554 | 586 | 30,100 | 0.42 | 0.36 | 0.70 |
| DsRed.T3 | 560 | 587 | 49,500 | 0.59 | 0.83 | 1.3 |
| DsRed.T4 | 555 | 586 | 30,300 | 0.44 | 0.38 | 0.71 |

[a]"Relative to wild-type DsRed, the other variants contain the following substitutions, where P(−4)L indicates a codon change in the polylinker upstream of the start codon."
DsRed2: R2A, K5E, K9T, V105A, I161T, S197A.
DsRed.T1: P(−4)L, R2A, K5E, N6D, T21S, H41T, N42Q, V44A, C117S, T217A.
DsRed.T3: P(−4)L, R2A, K5E, N6D, T21S, H41T, N42Q, V44A, A145P.
DsRed.T4: P(−4)L, R2A, K5E, N6D, T21S, H41T, N42Q, V44A, A145P, T217A.
[b]Brightness is determined by the product of the extinction coefficient and the quantum yield. Relative brightness is calculated by defining the brightness of DsRed1 as 1.00.
[c]The half-times for maturation were estimated graphically using the experimental protocol of FIG. 2. Values listed are the averages from two separate experiments; for each DsRed variant, the numbers obtained in the two experiments were within 15% of one another.

A previous study of wild-type DsRed reported a similar quantum yield but a higher extinction coefficient of 75,000 $M^{-1} cm^{-1}$; the reason for this discrepancy is unclear. DsRed2 shows slight reductions in both extinction coefficient and quantum yield, resulting in a relative brightness of 0.68 compared to DsRed1 (Table 1). DsRed.T3 is nearly as bright as DsRed1. However, DsRed.T1 and DsRed.T4 are dimmer, with relative brightnesses of 0.36-0.38 compared to DsRed1. To quantify the maturation kinetics of the DsRed variants, an in vivo pulse-chase analysis with *E. coli* cultures growing at 37° C. (FIG. 2) was performed. After a 30 min pulse of induction, protein synthesis inhibitors were added, and samples of the cultures were taken at various chase times. The average cellular fluorescence for each sample was measured by flow cytometry using a 488 nm excitation laser.

Figure 2:
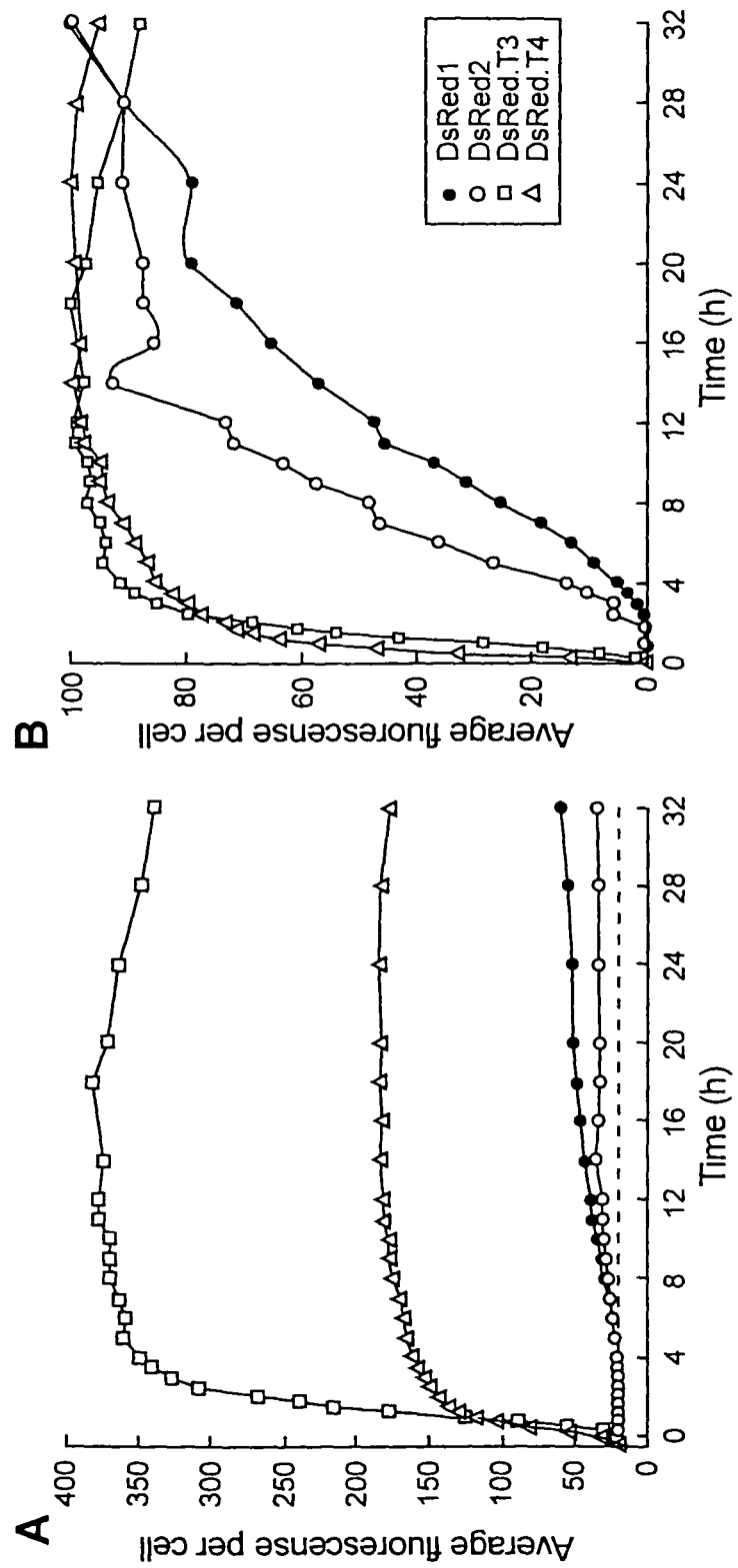
FIG. 2. Maturation kinetics of DsRed variants. Logarithmically growing E. coli cultures were treated with the inducer isopropyl β-D-thiogalactopyranoside (IPTG) for 30 min to generate a pulse of expression for each variant. A chase was then initiated (at time 0 on the graphs) by adding protein synthesis inhibitors and continuing the 37° C. incubation. Aliquots of the cultures were removed at the indicated times and subsequently analyzed by flow cytometry to determine the average intensity of red fluorescence per cell. The background fluorescence (dashed line) was measured using cells carrying the empty pQE81 plasmid. Plotted on the two graphs are (A) the raw fluorescence values, or (B) the values obtained by subtracting the fluorescence present at time 0 and normalizing to a maximum signal of 100% for each DsRed variant. A slight decline at later time points in the average fluorescence values for DsRed.T3 and DsRed.T4 probably reflects cell lysis. In a control culture, protein synthesis inhibitors were added simultaneously with IPTG to cells carrying the DsRed.T3 expression plasmid; as expected, those cells remained nonfluorescent (data not shown). Immunoblotting indicated that during the chase period, the amount of DsRed2, DsRed.T3, and DsRed.T4 protein in the cultures remained essentially constant, whereas the amount of DsRed1 protein progressively declined to about half of its initial level (data not shown).

FIG. 2A shows the raw data, while FIG. 2B shows the data normalized to a maximal fluorescence of 100%. Under these conditions, DsRed1 matures with a half-time of approximately 11 h, although accurate measurements are difficult with DsRed1 because the fluorescence values do not reach a plateau (FIG. 2) and because some of the DsRed1 protein is degraded during the chase period (data not shown). DsRed2 matures somewhat faster, with a half-time of approximately 6.5 h. The rates of fluorescence acquisition for DsRed1 and DsRed2 increase after a pro-nounced lag phase, indicating that multiple slow steps are involved. DsRed.T3 matures with a brief lag phase and half-time of approximately 1.3 h.

DsRed.T4 and DsRed.T1 mature with no detectable lag phase and with half-times of .0.7 h, about 15-fold faster than DsRed1 (FIG. 2, and data not shown). With this pulse-chase protocol, the different DsRed variants reproducibly showed distinct plateau values of average cellular fluorescence (FIG. 2A). The highsignal from DsRed.T3 can be explained by the relatively strong excitation of this protein at 488 nm (see FIG. 1B). DsRed1, DsRed2, and DsRed.T4 all have similarfluorescence spectra, yet the plateau fluorescence of DsRed.T4-expressing cells is 4-fold higher than that of DsRed1-expressing cells and 10-fold higher than that of DsRed2-expressing cells. This result is surprising because purified dsRed.T4 is less bright than DsRed1 or DsRed2 (Table 1). We speculate that immature DsRed1 is unstable in *E. coli*, and that this problem is exacerbated with DsRed2, so that a large fraction of the newly synthesized DsRed1 and DsRed2 molecules are lost through aggregation and/or degradation. Consistent with this idea, a previous study reported that most of the newly synthesized DsRed1 molecules are degraded in *E. coli* or *Drosophila* cells. Interestingly, DsRed2 gives a brighter fluorescence signal than DsRed1 in mammalian cells suggesting that the efficiency of expression for a given DsRed variant may be cell type specific.

Figure 3:
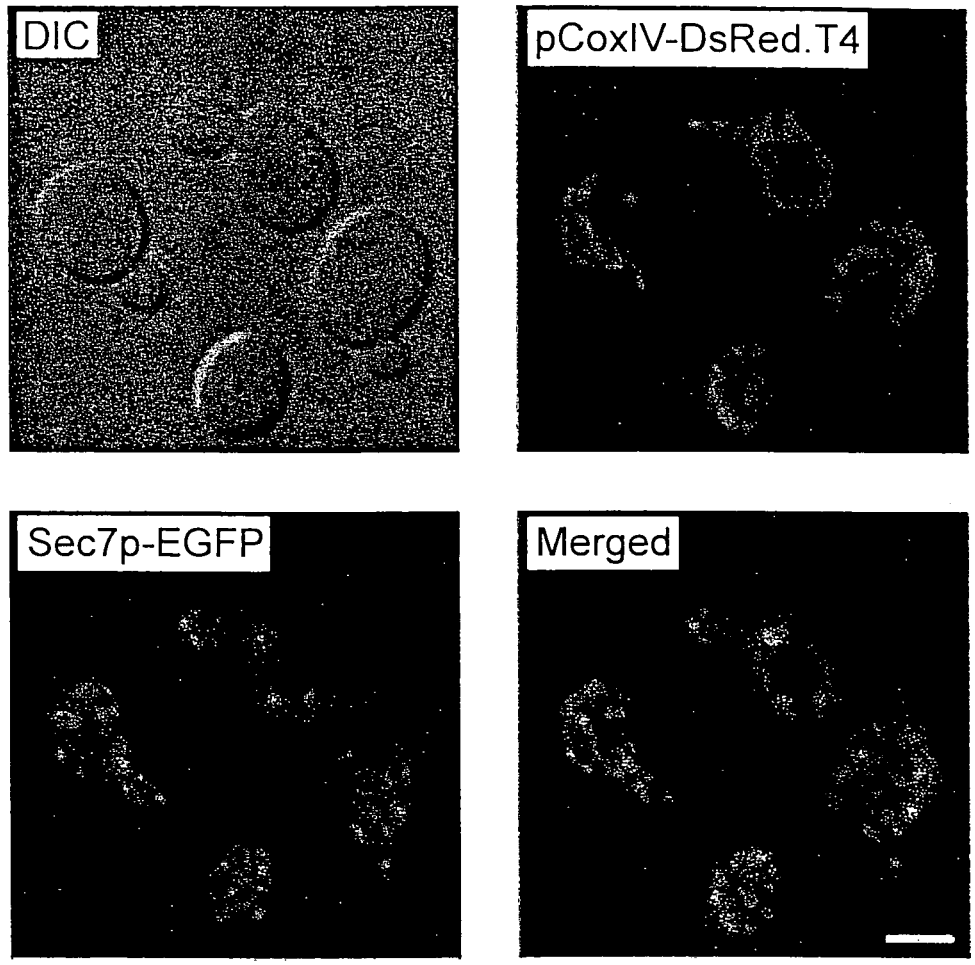
FIG. 3. Simultaneous visualization of DsRed.T4 and EGFP in yeast. DsRed.T4 was targeted to the mitochondrial matrix of Saccharomyces cerevisiae by fusion to the presequence of Cox4p. The pCox4-DsRed.T4 fusion protein was produced in a strain that also contained Sec7p-eGFP, a marker for Golgi cisternae. Cells from a logarithmically growing culture were imaged using either a Texas Red filter set (red) or an EGFP filter set (green). In addition, the cells were visualized by differential interference contrast (DIC) microscopy. As shown in the merged image, the DsRed.T4 and EGFP signals are easily resolved. Scale bar, 2 μm.

The benefits of accelerated maturation should be particularly evident when the DsRed variants are produced in a rapidly growing organism. To test this prediction, we targeted different DsRed variants to yeast mitochondria. The parental yeast strain also contained an EGFP-tagged marker for *Golgi cisternae*. With mitochondrially targeted DsRed1, the fluorescence was extremely faint in cells from growing cultures, and only became readily visible in a subset of the cells once the cultures reached stationary phase (data not shown). By contrast, mitochondrially targeted DsRed.T4 consistently gave a strong fluorescence signal in cells from growing cultures (FIG. 3). As shown in the merged image, we observed no detectable bleed-through of DsRed.T4 fluorescence into the green channel or of EGFP fluorescence into the red channel. Similar results were obtained with mitochondrially targeted DsRed.T3 (data not shown). However, with other fusion constructs we found that when a large amount of DsRed.T3 was concentrated in a small region of the cell, some bleed-through occurred into the green channel (not shown). Therefore, DsRed.T4 is the protein of choice for obtaining a clean separation of red and green fluorescence signals.

These results confirm that random mutagenesis followed by screening is a powerful method for creating improved fluorescent proteins. Our key finding is that Asn42 substitutions such as N42Q dramatically accelerate chromophore formation.

A side effect of Asn42 substitutions is a pronounced increase in blue excitation and green emission (FIG. 1A). Mature wild-type DsRed appears to be an equilibrium mixture of a red species and a green species, and the Asn42 substitutions evidently shift the equilibrium to yield a higher percentage of the green species. By introducing a series of additional substitutions into the N42Q background, we could suppress nearly all of the blue excitation and green emission that were conferred by N42Q while preserving the rapid maturation (FIG. 1 and Table 1).

Another improvement over wild-type DsRed was achieved by decreasing the net charge near the N terminus. The resulting DsRed variants show reduced aggregation in vitro (see below) and in vivo. Wild-type DsRed is unusually basic, with a predicted pI of 8.0, and probably associates nonspecifically with anionic cellular components. In addition, basic patches on the surface of a DsRed tetramer may interact with acidic patches on a second tetramer to cause higher-order aggregation. This interaction of DsRed with other macromolecules is evidently reduced by eliminating the cluster of positive charges near the N terminus.

The end result of our work is a pair of optimized variants termed DsRed.T3 and DsRed.T4. DsRed.T3 matures rapidly, and the purified protein is nearly as bright as mature wild-type DsRed (Table 1), making this variant well suited to single-color imaging of red fluo-rescence. DsRed.T3 has a higher peak of blue excitation and a slightly higher peak of green emission than wild-type DsRed (FIG. 1B), resulting in some contamination of the GFP signal in dual-color experiments. However, this contamination is usually minor. The enhanced blue excitation of DsRed.T3 can actually be advantageous, for example, if the fluorescence is being excited by a 488 nm laser (FIG. 2). DsRed.T4 has fluorescence spectra very similar to those of wild-type DsRed (FIG. 1B) and yields negligible contamination of the GFP signal (FIG. 3). Although purified DsRed.T4 is only about half as bright as DsRed.T3, this effect is partially offset in vivo because DsRed.T4 matures nearly twice as fast as DsRed.T3 (Table 1). Thus, DsRed.T4 is probably the best variant for most applications. DsRed.T1 is essentially identical to DsRed.T4 (Table 1),except that DsRed.T1 lacks cysteine residues and therefore might fold more efficiently in the oxidizing environment of the secretory pathway.

DsRed.T4 is a suitable template for further mutagenesis to produce additional variants.

The generation of new DsRed variants is likely to involve both random and directed mutagenesis. For directed mutagenesis studies, it is worth noting that five of the substitutions present in DsRed.T4 (R2A, H41T, N42Q, A145P, and T217A) replace a given residue with a residue that is more generally conserved in the family of DsRed homologs. Thus, sequence comparisons between DsRed and its relatives can suggest mutations that are likely to produce useful variants.

IV. Rapidly Maturing Variants of the *Discosoma* Red Fluorescent Protein (DsRed)"

This section describes the multi-step mutagenesis strategy that was used to obtain the optimized DsRed variants. An overview is provided in Table 2.

One of the original N42H-containing mutants produced brighter colony fluorescence than the other two. This increased brightness was due to a second mutation: H41L. Residue 41 is a threonine in several homologues of DsRed, and we found that an H41T substitution gives slightly brighter colonies than H41L. In the context of N42Q, H41T causes no significant change in the properties of the purified protein (not shown) but appears to yield a further increase in the maturation rate. Thus, after Round 1 of the mutagenesis we had incorporated the two substitutions H41T and N42Q (Table 2). The Round 1 variant generates a diffuse high-molecular weight band when analyzed by nondenaturing SDS-PAGE (FIG. 4A), suggesting that it is still tetrameric.

Additional rounds of mutagenesis were under- taken to accelerate the maturation further. Using the Round 1 variant as a template, we obtained three mutants that produced brighter E. coli colonies after one day of growth. All three mutants contained the V44A substitution. In addition to accelerating chromophore formation, V44A reduces the blue excitation and green emission relative to the Round 1 variant (not shown). One of the three V44A mutants also contained a T21S substitution, which further diminishes the blue excitation and green emission (not shown). Thus, the Round 2 variant contained the four substitutions T21S, H41T, N42Q and V44A (Table 2). Round 3 of the muta- genesis produced several mutants with a further increase in colony fluorescence. Surprisingly, the relevant mutation did not alter the DsRed protein itself, but instead was a proline-to-leucine codon change at position −4 in the linker between the hexahistidine tag and the initiator methionine. This result indicates that sequences appended to the N terminus of DsRed can affect protein folding and/or chromophore maturation. The P(−4)L substitution was incorporated to yield the Round 3 variant (Table 2).

When purifying the fluorescent proteins, we noticed that DsRed and its variants were inefficiently extracted from E. coli cells under lysis conditions that extract most of the EGFP.

This observation fits with reports that DsRed aggregates within cells. Round 4 of the mutagenesis was designed to reduce this aggregation. We devised an assay in which mutant bacterial clones were grown in 96-well plates, lysed with a detergent buffer, and spun to separate the extracted proteins from the bacterial pellets. The mutants of interest showed an increased ratio of soluble to insoluble red fluorescence. Of the more than 25such mutant proteins identified, nearly all had a reduction in the net charge near the N terminus. After testing a number of mutant combinations, we incorporated the trio of substitutions R2A, K5E and N6D to yield the Round 4 variant (Table 2).

Figure 4:
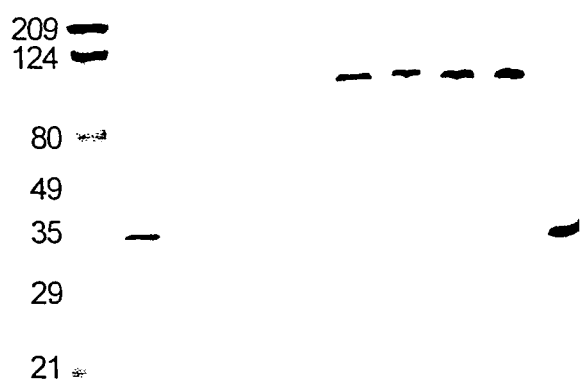
FIG. 4. Decreasing the net charge near the N terminus of DsRed reduces aggregation of the protein. (A) Nondenaturing SDS-PAGE of purified DsRed1 (WT), the Round 1 variant (R1), the Round 3 variant (R3), the Round 4 variant (R4), DsRed.T1 (T1), DsRed.T3 (T3) and DsRed.T4 (T4). 1 µg of each purified DsRed variant was mixed with SDS-containing sample buffer on ice and immediately electrophoresed at 4° C. in a 10% poly-acrylamide gel, followed by staining with Coomassie Blue. WT* and T4*: Additional aliquots of DsRed1 and DsRed.T4 were denatured by boiling prior to electrophoresis. MW: broad range prestained protein standard (Bio-Rad). (B) To measure the solubilities of the fluorescent proteins in E. coli, cells carrying pREP4 plus pQE31-based expression vectors encoding DsRed1, DsRed2, the Round 3 variant, the Round 4 variant, or EGFP were grown to an $OD_{600}$ of 0.5, induced with IPTG for 7 h, then lysed with B-PER II and centrifuged for 20 min at 27,000×g. Equivalent amounts of the pellet and supernatant fractions were subjected to SDS-PAGE followed by immunoblotting with an anti-hexahistidine monoclonal antibody (Qiagen). The bound antibody was detected using the ECL-Plus kit (Amersham) and a Molecular Dynamics Storm 860 phosphorimager. For each fluorescent protein, a dilution series from the bacterial extract was analyzed, and a sample within the linear range for the detection system was chosen. The percentage of each protein in the supernatant fraction was then quantified. Plotted are the average values from two separate experiments; for each fluorescent protein, the numbers obtained in the two experiments were within 10% of one another.
Figure 4:
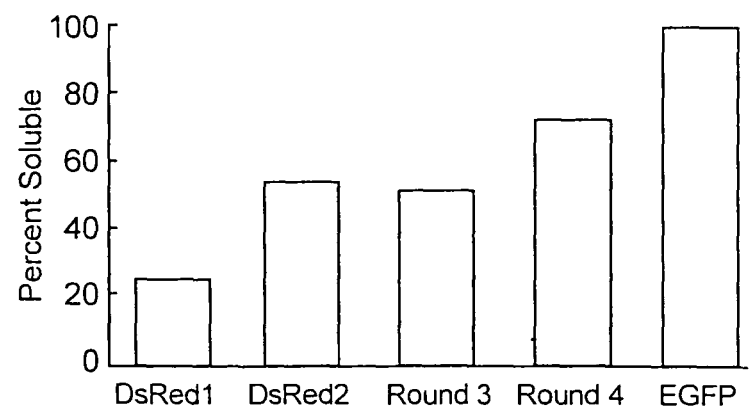

To compare the solubilities of the different DsRed variants, we expressed each protein in E. coli, lysed the cells in detergent buffer, and quantified the percentage of the protein molecules that were extracted (FIG. 4B). Virtually 100% of the EGFP molecules are solubilized under these conditions. Only ~25% of the DsRed1 molecules are solubilized. DsRed2 is substantially more soluble (~55%) than DsRed1. The Round 3 variant is also more soluble (~52%) than DsRed1, but the Round 4 variant shows even higher solubility (~73%). When analyzed by nondenaturing SDS-PAGE, the Round 3 variant generates a diffuse band that may reflect the formation of higher-order oligomers whereas the Round 4 variant generates a sharp band at the position predicted for a tetramer (FIG. 4A). These results suggest that reducing the net charge near the N terminus of DsRed suppresses aggregation of the tetramers.

TABLE 2

Relevant mutations in DsRed

| Round of mutagenesis | Goal of mutagenesis | Mutations obtained or examined | Final mutations incorporated |
| --- | --- | --- | --- |
| 1 | Accelerating maturation | N42H, N42Q H41L, H41T | N42Q H41T |
| 2 | Accelerating maturation, reducing green emission | V44A T21S | V44A T21S |
| 3 | Accelerating maturation | P(−4)L | P(−4)L[a] |
| 4 | Enhancing solubility | R2H, R2L, R2A, K5E, K5Q, K5M N6D | R2A[b] K5E N6D |
| 5 | Reducing green emission | T217A | T217A[c] |
| 6 | Reducing green emission | C117S, C117A A145P, A145S | C117S[d] A145P[d] |

[a]The proline codon at position −4 relative to the start codon was contributed by the multiple cloning site in the pDsRed1-N1 vector.
[b]The R2A substitution also eliminates the extra valine codon that is present after the start codon in DsRed1.
[c]T217A is present in DsRed.T1 and DsRed.T4, but not in DsRed.T3.
[d]DsRed.T1 contains C117S but not A145P, whereas DsRed.T3 and DsRed.T4 contain A145P but not C117S.

The Round 4 variant still gives a noticeable bleed-through fluorescence with GFP filter sets (not shown). Therefore, we undertook Round 5 of the mutagenesis to reduce the green emission further. Flow cytometry was used to select E. coli cells that showed bright fluorescence with an increased ratio of red to green emission. All seven of the resulting mutants contained a T217A substitution. In addition to reducing the blue excitation and green emission, T2176A reverses the slight spectral red-shift observed with N42Q (see FIG. 4A in the main text). T217A was incorporated to yield the Round 5 variant (Table 2).

Finally, we took advantage of fortuitous observations from unrelated mutagenesis experiments. The C117S substitution further reduces the blue excitation and green emission. Thus, the optimized variant designated DsRed.T1 contains the following substitutions: P(−4)L, R2A, K5E, N6D, T21S, H41T, N42Q, V44A, C117S and T217A. The A145P substitution is similar to C117S in its effect on the fluorescence spectra, but in some DsRed mutant backgrounds, colony fluorescence is slightly decreased by C117S and slightly increased by A145P (not shown). Therefore, we created a second optimized variant called DsRed.T4, which is identical to DsRed.T1 except that the C117S substitution has been replaced with A145P. Subsequent analysis revealed that the advantages conferred by T217A are accom-panied by a modest decrease in brightness, so we created a third optimized mutant called DsRed.T3, which is identical to DsRed.T4 except that DsRed.T3 lacks the T217A substitution.

The blue excitation and green emission are reduced by the T21S, V44A, C117S, A145P and T217A substitutions. Val44 and Thr217 face the interior of the DsRed protein and are close to residue 42, indicating that the V44A and T217A substitutions relieve the steric constraints caused by N42Q. By contrast, Thr21, Cys117 and Ala145 face the surface of the DsRed monomer, so T21S, C117S and A145P are indicated as altering the overall packing of the protein. T21S and A145P may influence DsRed structure by modifying the tetramer interfaces.

It is evident from the above results and discussion that the present invention provides an important new class of fluorescent proteins that rapidly mature. As such, the subject invention represents a significant contribution to the art.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A polynucleotide encoding a fluorescent mutant of wild-type DsRed comprising an amino acid substitution at amino acid position 42 of SEQ ID NO:2, wherein the mutant matures more rapidly than the wild-type DsRed.

2. The polynucleotide of claim 1, wherein the mutant further comprises a mutation in at least one amino acid position selected from the group consisting of amino acid residues 2, 5, 6, 21, 41, 44, 117, 145, and 217 of SEQ ID NO: 2.

3. The polynucleotide of claim 1, wherein the mutant comprises the mutation N42Q.

4. The polynucleotide of claim 1, wherein the mutant comprises the mutation N42H.

5. The polynucleotide of claim 2, wherein the mutant comprises a mutation at amino acid position 41 of SEQ ID NO: 2.

6. The polynucleotide of claim 5, wherein the mutation at amino acid position 41 of SEQ ID NO: 2 is selected from the group consisting of H41T and H41L.

7. The polynucleotide of claim 5, wherein the mutant further comprises a mutation at amino acid position 44 of SEQ ID NO: 2.

8. The polynucleotide of claim 7, wherein the mutation at amino acid position 44 of SEQ ID NO: 2 is V44A.

9. The polynucleotide of claim 2, wherein the mutant comprises a mutation at amino acid position 44 of SEQ ID NO: 2.

10. The polynucleotide of claim 9, wherein the mutation at amino acid position 44 of SEQ ID NO: 2 is V44A.

11. The polynucleotide of claim 1, wherein the mutant comprises mutations H41T, N42Q, and V44A of SEQ ID NO:2.

12. The polynucleotide of claim 2, wherein the mutant further comprises mutation T21S.

13. The polynucleotide of claim 2, wherein the mutant further comprises a mutation that results in a reduction in the net charge near the N terminus.

14. The polynucleotide of claim 13, wherein the mutation that results in a reduction in the net charge near the N terminus is selected from the group consisting of R2H, R2L, R2A, K5E, K5Q, K5M, and N6D.

15. The polynucleotide of claim 14, wherein the mutant comprises mutations R2A, K5E, and N6D.

16. The polynucleotide of claim 15, further comprising mutations T21S, H41T, N42Q and V44A.

17. The polynucleotide of claim 16, further comprising mutations C117S and T217A.

18. The polynucleotide of claim 16, further comprising mutation A145P.

19. The polynucleotide of claim 18, further comprising mutation T217A.

20. The polynucleotide of claim 2, wherein the mutant comprises mutation T217A.

21. The polynucleotide of claim 2, wherein the mutant comprises a mutation selected from the group consisting of A145P and A145S.

22. The polynucleotide of claim 2, wherein the mutant comprises a mutation selected from the group consisting of C117S and C117A.

23. A polynucleotide comprising the polynucleotide of claim 1 operably linked to a promoter.

24. A cell comprising the polynucleotide of claim 1.

25. A method of producing a fluorescent polypeptide comprising growing the cell of claim 24, whereby the polynucleotide is expressed to produce the fluorescent polypeptide.

26. A non-human transgenic organism comprising the polynucleotide of claim 1.

27. A kit comprising the polynucleotide of claim 1.

28. The polynucleotide of claim 1, wherein the fluorescent mutant further comprises amino acid substitutions at amino acid positions 2, 5, 6, 21, 41 and 44 of SEQ ID NO:2.

29. The polynucleotide of claim 1, wherein the fluorescent mutant is a fusion protein.

30. A method of detecting expression of a fusion protein, comprising obtaining expression of the polynucleotide of claim 29 and detecting fluorescence.

\* \* \* \* \*